(12) United States Patent
Dissanayake et al.

(10) Patent No.: US 11,416,988 B2
(45) Date of Patent: Aug. 16, 2022

(54) APPARATUS AND METHOD FOR VISUALIZING VISUALLY IMPERCEIVABLE COSMETIC SKIN ATTRIBUTES

(71) Applicant: The Procter & Gamble Company, Cincinnati, OH (US)

(72) Inventors: Dissanayake Mudiyanselage Mahathma Bandara Dissanayake, Singapore (SG); Naoki Miyamoto, Kobe (JP); Linda Shushan Lim, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 109 days.

(21) Appl. No.: 16/856,305

(22) Filed: Apr. 23, 2020

(65) Prior Publication Data
US 2020/0342594 A1     Oct. 29, 2020

Related U.S. Application Data

(60) Provisional application No. 62/837,208, filed on Apr. 23, 2019.

(51) Int. Cl.
*G06K 9/00*     (2022.01)
*G06T 7/00*     (2017.01)
(Continued)

(52) U.S. Cl.
CPC ............ *G06T 7/0012* (2013.01); *A61B 5/441* (2013.01); *A61B 5/7435* (2013.01); *G16H 50/20* (2018.01);
(Continued)

(58) Field of Classification Search
None
See application file for complete search history.

(56) References Cited

U.S. PATENT DOCUMENTS

| 6,424,973 | B1 | 7/2002 | Baclawski |
| 6,463,433 | B1 | 10/2002 | Baclawski |
| (Continued) |

FOREIGN PATENT DOCUMENTS

| CN | 104299011 A | 1/2015 |
| JP | 2009082338 A | 4/2009 |
| (Continued) |

OTHER PUBLICATIONS

Bargh, Becky, "Selfie skin analysis found to boost customer conversion by 50%", Retrieved from: https://www.cosmeticsbusiness.com/news/article_page/Selfie_skin_analysis_found_to_boost_customer_conversion_by_50/144771, Jul. 6, 2018, 3 Pages.

(Continued)

*Primary Examiner* — Wei Wen Yang
(74) *Attorney, Agent, or Firm* — Alexandra S. Anoff

(57) ABSTRACT

A method of visualizing at least one cosmetic skin attribute of a subject is provided. The method includes obtaining a digital image of the face of a person, defining a plurality of tiles across the image, analyzing each of the defined tiles for the at least one cosmetic skin attribute, assigning a single degree of indicium uniquely to each tile based on the analyzed at least one cosmetic skin attribute of the tile, and displaying at least some of the tiles so that a user can visualize the cosmetic skin attribute. The displayed tiles may be selected to indicate to user a cosmetic skin attribute condition that is better relative to the non-displayed tiles, based on the analyzed skin attribute.

15 Claims, 17 Drawing Sheets

(51) Int. Cl.
  *G16H 50/30* (2018.01)
  *G16H 50/20* (2018.01)
  *A61B 5/00* (2006.01)

(52) U.S. Cl.
  CPC ... *G16H 50/30* (2018.01); *G06T 2207/10024* (2013.01); *G06T 2207/20081* (2013.01); *G06T 2207/30088* (2013.01); *G06T 2207/30201* (2013.01)

(56) References Cited

U.S. PATENT DOCUMENTS

| | | |
|---|---|---|
| 6,571,003 B1 | 5/2003 | Hillebrand et al. |
| 9,111,132 B2 | 8/2015 | Aoki |
| 9,665,945 B2 | 5/2017 | Wang |
| 9,747,685 B2 | 8/2017 | Miyamoto |
| 2006/0228037 A1 | 10/2006 | Simon et al. |
| 2008/0080755 A1 | 4/2008 | Payonk et al. |
| 2009/0080727 A1 | 3/2009 | Cotton et al. |
| 2010/0158330 A1 | 6/2010 | Lavi et al. |
| 2010/0284610 A1 | 11/2010 | Yoshikawa |
| 2011/0286643 A1 | 11/2011 | Kislal |
| 2017/0270593 A1 | 9/2017 | Sherman |
| 2018/0350071 A1 | 12/2018 | Purwar |
| 2019/0377969 A1* | 12/2019 | Kuo ............ G06K 9/00268 |
| 2020/0170564 A1* | 6/2020 | Jiang ............ A61B 5/7267 |
| 2020/0342213 A1 | 10/2020 | Dissanayake |

FOREIGN PATENT DOCUMENTS

| | | |
|---|---|---|
| KR | 100408829 B1 | 1/2004 |
| KR | 101701210 B1 | 2/2017 |

OTHER PUBLICATIONS

AA01345M PCT Search Report and Written Opinion for PCT/US2020/029422 dated Jul. 3, 2020, 13 pages.
"The Revieve Digital Skincare Advisor", Retrieved from: https://www.youtube.com/watch?v=OuBWSSO0mNk, Sep. 9, 2017, 1 Page.
"VISIA Redefining the Vision of Skin Care", Retrieved from: https://www.canfieldsci.com/imaging-systems/visia-complexion-analysis/. Retrieved Date: May 6, 2021, 10 Pages.
All Office Actions; U.S. Appl. No. 16/856,336.

* cited by examiner

APPARATUS AND METHOD FOR VISUALIZING VISUALLY IMPERCEIVABLE COSMETIC SKIN ATTRIBUTES

TECHNICAL FIELD

The present invention relates to systems and methods for visualizing a cosmetic skin attribute.

BACKGROUND

Consumers seek to improve their physical appearance through the use of cosmetics and skin care treatments. As a result, there is an extremely large choice of available products for consumers to choose from. Often, individual consumers find it difficult to determine which products to apply and how to apply them to achieve best results when taking into account the individual's own personal skin type and skin attributes, and potentially different or changing skin attributes. This problem is compounded as the individual's skin changes over time and/or beauty trends change over time. Beauty counselors at retail cosmetics counters are often charged with identifying skin attributes of a client in need of treatment. Once the skin attribute(s) are identified, the counselor will communicate the type, quantity, and location of those skin attribute(s) to the client for discussion. Finally, the counselor recommends skin care products and application techniques aimed at improving the appearance of the identified skin attributes and demonstrate the improvement to the consumer. Much of this approach depends upon the subjective judgment and/or visual acuity of the counselor.

As a growing population of digital savvy consumers, particularly those of a younger demographic, tend to utilize computing devices to interact with one another and make purchase decisions for skin and beauty care products online instead of seeking consultation with a traditional beauty counselor. Some of these consumers believe there is a great level of objectivity that can be achieved with digital tools and such, recommendations from a digital source are more credible to this consumer segment. Numerous attempts have been made to enable such consumers to perform individual skin analysis by analyzing a digital image of themselves (e.g., a "selfie") using a computer modeling/algorithms. The results provided by the computer model can then be used to provide a consumer with the location and type of visually perceivable skin attributes (e.g., visible age spots, visible lines and wrinkles) and a subsequent product recommendation/usage instruction.

One way of indicating/marking these visually perceivable skin attributes to the consumer is through "heat maps" to visualize the face and skin attribute(s) thereof. However, there is typically a lot of information for the consumer to comprehend. This may not be as challenging as problem with a visually perceivable skin attribute because the consumer can use the visually perceivable attribute as point of reference or a target of skin care treatment. However, the problem is considerably exacerbated when the skin attribute is visually imperceivable one. This is particularly true in the younger demographic of consumers that may not have, or have a minimal amount of, visually perceivable attributes. Therefore, there is a need to quickly and easily identify the visually imperceivable attribute and its location on the face, particularly when there are more than one such visually imperceivable attribute, and even more so in a younger consumer demographic that typically lacks many perceivable skin attributes.

There is a growing body of research that suggests that some visually imperceivable skin attributes become a prelude to visually perceivable ones. To this end, if the consumer can identify these visually imperceivable skin attributes early in her life and conduct preventive skin treatment to these attributes, there is an increased likelihood of delaying and/or mitigating the occurrence and/or delaying the onset of undesirable visually perceivable skin attributes from forming later in time.

A variety of skin assessment digital tools have been developed to meet the needs of consumers in the digital age so as to provide information on the above skin attributes, consumers have all been subject to a massive information overload and this makes the process of understanding the information challenging for many consumers in a short amount of time especially in the context of cosmetic skin attribute conditions, e.g. "what is my existing skin condition, and what can I do to improve it?". However, consumers tend to view the assessment information on portable devices such as mobile phones or have a limited time to understand the assessment information. As a result, consumers may become quickly overwhelmed if a vast amount of information is displayed and this leads to "information overload". Information overload can lead to a situation where, due to an excess of information, the consumer is no longer understanding the information or be in a position to assess what needs to be done to improve his or her skin condition. In such situations, the consumers may stop using the digital tools which generate information overload for the consumers.

Accordingly, there is a need for methods and systems that provide consumers with a way to identify one or more skin attributes, and display the location of these attributes on the face of the consumer in a simple way so as to allow the consumer to understand his or her cosmetic skin attribute, and obtain targeted and effective treatment for improving a condition of the cosmetic skin attribute.

SUMMARY

The present invention relates to a method of visualizing at least one cosmetic skin attribute of a subject, the method comprising the steps of:
a) obtaining a first digital image of at least a portion of a face of the subject, wherein the first digital image is selected from at least an area of an input image of the face;
b) defining a plurality of tiles across the obtained first digital image;
c) analyzing the first digital image for each of the defined plurality of tiles for the at least one cosmetic skin attribute;
d) assigning a single degree of indicium uniquely to each tile, of the defined plurality of tiles, based on the analyzed at least one cosmetic skin attributes of the tile; and
e) displaying at least some of the plurality of tiles each having uniquely assigned single degree of indicium to visualize at least one cosmetic skin attribute;
wherein the displayed at least some of the plurality of tiles displays a cosmetic skin attribute condition that is better relative to a cosmetic skin attribute condition of a non-displayed tile of the plurality of tiles based on the analyzed at least one cosmetic skin attribute of the tile.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

DETAILED DESCRIPTION

Figure 1:
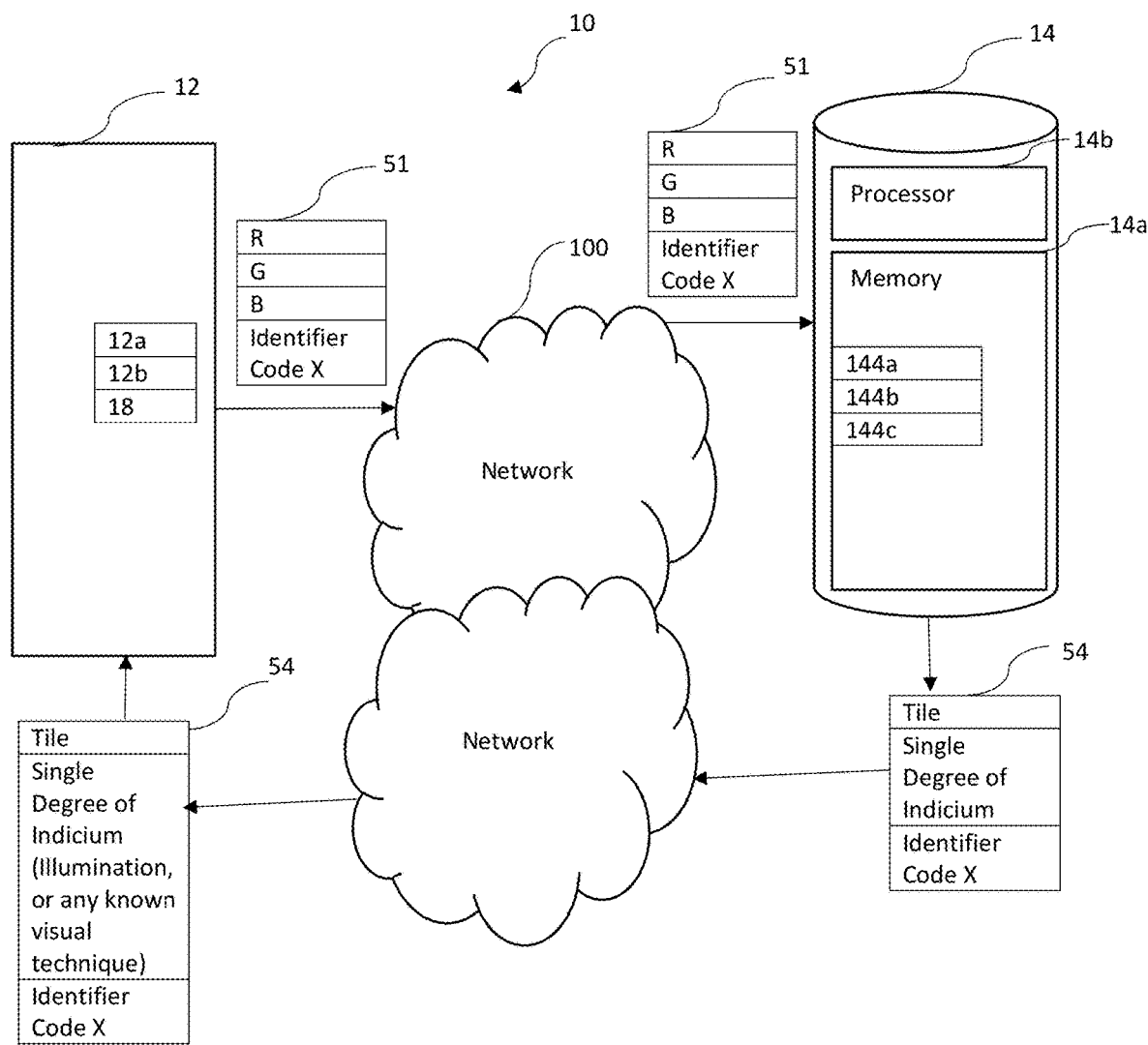
FIG. 1 is a diagram illustrating an exemplary system for visualizing at least one cosmetic skin attribute over a network according to the present invention.

It is known that when the skin is subjected to stress (caused by UV, chronological aging, mental stress, environmental factors), skin will be damaged at various levels including DNA level, cellular level and tissue level. Such damages to the skin can result in skin imperfections. Presence of these skin imperfections significantly impact on optics of the skin such as described in the following examples:

If the stratum corneum is dry (winter/air condition), light will reflect more from the surface (surface reflection) enhancing skin micro texture which cause lines on the skin.

If the dermis is damaged (UV), less light will scatter at dermis (also known as dermis-scattering) and light will penetrate skin (less subsurface reflection). When there is less demis-scattering, and the skin appears darker as a result.

If skin is exposed to chronic UV, skin produces more melanin. Melanin absorbs light reducing subsurface reflection and hence skin appears darker.

The above skin imperfections manifest as visually imperceivable signals of poor skin quality to the consumers eye. Consumers may consider these imperfections as impurities at a subconscious level, but, are not able to take action to improve the imperfections because of lack of conscious knowledge. If the skin is subject to chronic stress and/or untreated, these visually imperceivable impurities may eventually lead to visible and perceivable phenotypes (pigmented spots, wrinkles, sagging).

The present invention relates to a method, apparatus and system for visualizing at least one cosmetic skin attribute of a subject and a graphical user interface. The cosmetic skin attribute may comprise visually perceivable cosmetic skin attributes or visually imperceivable cosmetic skin attributes.

The method comprising the steps of;
a) obtaining a first digital image of at least a portion of a face of the subject, wherein the first digital image is selected from at least an area of an input image of the face;
b) defining a plurality of tiles across the obtained first digital image;
c) analyzing the first digital image for each of the defined plurality of tiles for the at least one cosmetic skin attribute;
d) assigning a single degree of indicium uniquely to each tile, of the defined plurality of tiles, based on the analyzed at least one cosmetic skin attributes of the tile; and e) displaying at least some of the plurality of tiles each having uniquely assigned single degree of indicium to visualize at least one cosmetic skin attribute;

wherein the displayed at least some of the plurality of tiles displays a cosmetic skin attribute condition that is better relative to a cosmetic skin attribute condition of a non-displayed tile of the plurality of tiles based on the analyzed at least one cosmetic skin attribute of the tile.

It has been surprisingly found that by only displaying some of the tiles which displays a cosmetic skin attribute condition that is better relative to a cosmetic skin attribute condition of a non-displayed tile of the plurality of tiles, consumers can better understand the condition of the cosmetic skin attribute easily, and therefore make an informed decision to seek treatment for improving a condition of the cosmetic skin attribute.

In particular, a technical effect of having non-displayed tiles minimizes "information clutter" and "information overload" on a single display, especially displaying on an electronic portable device that is of a small form factor, such as for example, a mobile phone. A further technical effect is that computing resources needed for generating displays in a short amount of time can be reduced, and this results in a better user experience when using the present invention (for example as a native application on a mobile phone, or through a web application accessed through the mobile phone.

Prior to describing the present invention in detail, the following terms are defined and terms not defined should be given their ordinary meaning as understood by a skilled person in the relevant art.

"Entropy" as used herein refers to a Shannon entropy (E) of a discrete random distribution (p(x)) and is defined by the following equation:

$$E(p) = -\sum_x p(x) \times \log p(x)) \quad (1)$$

wherein p(x) is the distribution of grey levels

E(p) represents the amount of information in a digital image or a color channel image in a color system after conversion of the digital image to the color channel image.

"Entropy statistics" as used herein refers to a statistical method that uses entropy as a descriptive statistic for analyzing digital images or color channel images. In a non-limiting example wherein the digital image is an RGB image, entropies for each R (red), G (green) and B (blue) channel can be calculated separately. The entropy value of an image can be calculated by calculating at each pixel position (i,j) the entropy value of the pixel-values within a 2-dimensional region centered at (i,j). The 2-dimensional region may be a part of a color channel image. Programming software packages such as Python may be used to calculate the entropy value.

"Cosmetic skin attribute" as used herein includes all skin attributes that provide a visual/aesthetic effect on an area of the human body or impact skin appearance and/or feel. Some non-limiting examples of a cosmetic skin attribute may include skin topography, skin elasticity, skin tone, skin pigmentation, skin texture, skin pores, cosmetic skin inflammation, skin hydration, skin sebum level, acne, moles, skin radiance, skin shine, skin dullness, uneven tone, or skin barrier. It will be appreciated by a skilled person that the above cosmetic skin attributes are standard terms, and a corresponding definition of the cosmetic skin attribute may be found in the following published references namely, "Handbook of cosmetic science and technology, $3^{rd}$ edition, editors Andre O. Barel, Marc Paye, Howard I. Maiback, CRC Press, 2009", "Cosmetic Science and Technology-Theoretical Principles and Applications, editors Kazutami Sakamoto Robert Y. Lochhead, Howard I. Maibach, Yuji Yamashita, Elsavier, 2017", "Cosmetic Dermatology: Products and Procedures, Editor(s): Zoe Diana Draelos, Blackwell Publishing Ltd, 2010". Cosmetic skin attributes do not include skin attributes related to medical conditions or underlying medical conditions.

"Imperceivable cosmetic skin attribute" as used herein refers to a cosmetic skin attribute that cannot be perceived or is imperceptible by the perceiver, i.e. a person, a user, or a human subject. Perceive derives from the word "Perception" which refers to the organization, identification, and interpretation of sensory information in order to represent and understand the presented information, or the environment. All perception involves signals that go through the nervous system, which in turn result from physical or chemical stimulation of the sensory system. For example, vision involves light striking the retina of the eye, smell is mediated by odor molecules, and hearing involves pressure waves. Perception is not only the passive receipt of these signals, but it is also shaped by the recipient's learning, memory, expectation, and attention. Perception can be split into two processes, i.e. process (1) that relates to processing the sensory input, which transforms these low-level information to higher-level information (e.g., extracts shapes for object recognition), and process (2) that relates processing which is connected with a person's concepts and expectations (or knowledge), restorative and selective mechanisms (such as attention) that influence perception. For example, a perceiver may see an object in process (1) but does not have the knowledge to perceive and recognize what the object represents/mean in process (2), and therefore may regard the object to be visually imperceivable.

"Visually imperceivable cosmetic skin attribute" as used herein includes all cosmetic skin attributes which are not detectable by an unaided eye or a cosmetic skin attribute detectable visually by a consumer but the consumer does not understand the cosmetic skin attribute, and therefore regarded as imperceivable cosmetic skin attributes. Some nonlimiting examples of a visually imperceivable cosmetic skin attribute that is not detectable visually by the unaided eye include cosmetic skin inflammation, skin sebum level, or any underlying cosmetic skin attribute.

"Unaided" as used herein means without assistance from diagnostic equipment.

"Tile" as used herein includes a unit, such as for example a pixel, that form a part of a digital image and accordingly "Tiles" form the whole of the digital image.

"Digital image data" as used herein includes image data obtained from an image obtaining device including but not limited to a digital camera, a photo scanner, a computer readable storage medium capable of storing digital images, and any electronic device including picture taking capabilities. Digital image data may also include color channel images which are converted from a RGB image into a color channel image in a color system.

"Single degree of indicium" as used herein includes all electronic visual representations including but not limited to a graphical symbol, a numerical value, a color code, illumination techniques and combinations thereof.

"Skin Attribute Index" as used herein refers to a score that can be calculated based on a mathematical formula or a model derived from statistical methods and data or a lookup table (an array of information). The Skin Attribute Index may be generated as a probability value indicative of a condition of the cosmetic skin attribute of the at least one portion of skin of the person relative to a defined population of people, preferably the Skin Attribute Index is generated as a function of the entropy value defined by F (Entropy Value), wherein said function is determined by a model established upon a training dataset wherein the training dataset comprises: (i) a plurality of color channel images of a the defined population of people, wherein each of the plurality of color channel images comprises facial skin of a person in the defined population of people, wherein the facial skin comprises the cosmetic skin attribute; (ii) an associated class definition based on the cosmetic skin attribute.

"L*a*b*" as used herein, refers to the commonly recognized color space specified by the International Commission on Illumination ("CIE"). The three coordinates represent (i) the lightness of the color (i.e., L*=0 yields black and L*=100 indicates diffuse white), (ii) the position of the color between magenta and green (i.e. negative a* values indicate green while positive a* values indicate magenta) and (iii) the position of the color between yellow and blue (i.e. negative b* values indicate blue and positive b* values indicate yellow).

"Chromophore mapping" as used herein, refers to the commonly recognized chromophore space for melanin and hemoglobin mapping and determining melanin or hemoglobin concentration which may be used as an indicator of overall skin tone. Mean melanin or hemoglobin may be calculated from the chromophore map data. Additionally, skin tone evenness can be determined by melanin or hemoglobin evenness (e.g. standard deviation) which also may be calculated from the chromophore map data.

"Skin purity" as used herein, appearance of the absence of skin imperfections in at least of portion of skin of a person. The skin imperfections include cosmetic skin attributes which impact irregular or non-uniform spectral properties composed of the surface reflection of the skin topographical morphology and/or the sub-surface reflection of skin chromophores such as melanin, haemoglobin and/or keratinocyte and fibroblast oriented cellular metabolites, and include but are not limited to skin radiance, skin tone or the like.

"Skin age" as used herein, means apparent age which refers to the age of skin of a person that is visually estimated or perceived to be, compared to norm age skin appearances, based on the physical appearances, preferably a face of the person, preferably at least a portion of a face of the person, more preferably, at least one region of interest (ROI) of the at least a portion of a face of the person, even more preferably, the at least one ROI is selected from the group consisting of: a skin region around the eye ("eye region"), a skin region around the cheek ("cheek region"), a skin region around the mouth ("mouth region"), and combinations thereof.

"Skin tone" as used herein, generally refers to the overall appearance of basal skin color or color evenness. Skin tone is typically characterized over a larger area of the skin. The area may be more than 100 mm2, but larger areas are envisioned such as the entirety of the facial skin or other bodily skin surfaces (e.g. arms, legs, back, hands, neck).

"Skin wrinkle" as used herein, generally refers to a fold, ridge or crease in the skin and includes but is not limited to fine lines, super fine lines, fine wrinkles, super fine wrinkles, wrinkles, lines. Skin wrinkle may be measured in terms of, for example, density and/or length.

"Skin radiance" as used herein, generally refers to an amount of light that the skin reflects, and, may be referred to as skin shine.

"Skin texture" as used herein, generally refers to the topology or roughness of the skin surface.

"Skin tension" as used herein, generally refers to the firmness or elasticity of the skin.

"Skin sebum level" as used herein, generally refers to an amount of sebum which is an oily or waxy matter secreted by sebaceous glands in the skin.

"Skin spots" as used herein, generally refers discoloration or uneven pigmentation (e.g. hyperpigmentation, blotchiness) of the skin. Skin spots may be evaluated in terms of, e.g. density, size, and/or degree of discoloration.

"Skin care product" as used herein, refers to a product that includes a skin care active and regulates and/or improves skin condition.

"Digital image" as used herein, refers to a digital image formed by pixels in an imaging system including but not limited to standard RGB, or the like and under images obtained under different lighting conditions and/or modes. Non-limiting examples of a digital image include color images (RGB), monochrome images, video, multispectral image, hyperspectral image or the like. Non-limiting light conditions include white light, blue light, UV light, IR light, light in a specific wavelength, such as for example light source emitting lights from 100 to 1000 nm, from 300 to 700 nm, from 400 to 700 nm or different combinations of the upper and lower limits described above or combinations of any integer in the ranges listed above. The digital image may be obtained from an image obtaining device including but not limited to a digital camera, a photo scanner, a computer readable storage medium capable of storing digital images, and any electronic device including picture taking capabilities.

In the following description, the system described is a system for visualizing a cosmetic skin attribute. Accordingly, the apparatus described is an apparatus for visualizing a cosmetic skin attribute, and the graphical user interface described is a graphical user interface for visualizing a cosmetic skin attribute. The graphical user interface may be further configured for providing a product recommendation to treat at least one cosmetic skin attribute.

In an exemplary embodiment, the system is a stand-alone imaging system (shown in FIG. 2) that is located at a retail cosmetics counter for the purpose of analyzing and recommending cosmetic and skin care products. However, it is contemplated that the system and the method may be configured for use anywhere, such as for example as shown in FIG. 1, through an electronic portable device comprising an image obtaining unit and a display, wherein the electronic portable device is connected to an apparatus for generating for display on a display, a graphical user interface for visualizing a cosmetic skin attribute through a network.

System

FIG. 1 is a schematic diagram illustrating a system 10 for visualizing a cosmetic skin attribute according to the present invention. The system 10 may include a network 100, which may be embodied as a wide area network (such as a mobile telephone network, a public switched telephone network, a satellite network, the internet, etc.), a local area network (such as wireless-fidelity, Wi-Max, ZigBee™, Bluetooth™, etc.), and/or other forms of networking capabilities. Coupled to the network 100 are a portable electronic device 12, and an apparatus 14 for generating for display on a display, a graphical user interface for visualizing a cosmetic skin attribute. The apparatus 104 is remotely located and connected to the portable electronic device through the network 100.

The portable electronic device 12 may be a mobile telephone, a tablet, a laptop, a personal digital assistant and/or other computing device configured for capturing, storing, and/or transferring a digital image such as a digital photograph. Accordingly, the portable electronic device 12 may include an input device 12a for receiving a user input, an image obtaining device 18 such as a digital camera for obtaining images and an output device 12b for displaying the images. The portable electronic device 12 may also be configured for communicating with other computing devices via the network 100. The portable electronic device 12 may further comprise an image processing device (not shown) coupled with said imaging obtaining device 18 for analyzing the obtained at least one color channel image using entropy statistics to obtain an entropy value and determining the cosmetic skin attribute of the at least one portion of skin of the person based on the entropy value. The image processing device preferably comprises a processor with computer-executable instructions. The portable electronic device 12 may further comprise a display generating unit (not shown, such as an electronic LED/LCD display) for generating a display to display content data describing the determined cosmetic skin attribute. The apparatus 14 may include a non-transitory computer readable storage medium 14a (hereinafter "storage medium"), which stores image obtaining logic 144a, image analysis logic 144a and graphical user interface (hereinafter "GUI") logic 144c. The storage medium 14a may comprise random access memory (such as SRAM, DRAM, etc.), read only memory (ROM), registers, and/or other forms of computing storage hardware. The image obtaining logic 144a, image analysis logic 144b and the GUI logic 144c define computer executable instructions. A processor 14b is coupled to the storage medium 14a, wherein the processor 14b is configured to, based on the computer executable instructions, for implementing a method 200 for visualizing a cosmetic skin attribute of a subject according to the present invention as described herein after with respect to process flow diagrams of FIG. 4A to 4C and the flowchart of FIG. 5.

Method

Figures 4A, 4B, 4C:
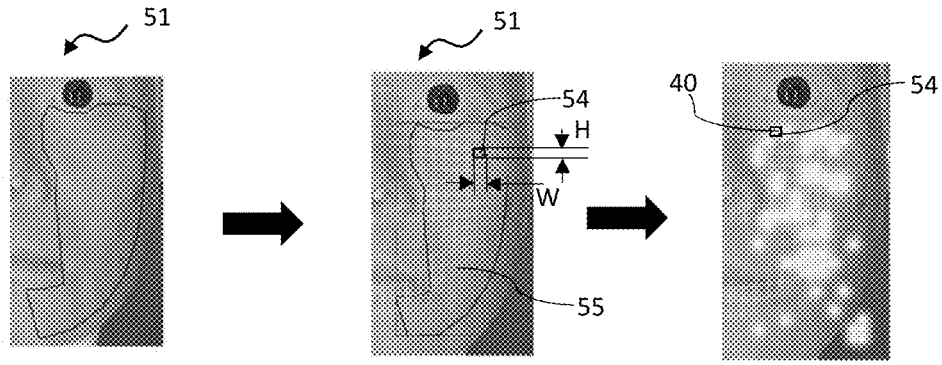
FIGS. 4A to 4C are a series of process flow diagrams illustrating a method of visualizing a cosmetic skin attribute according to the present invention.
Figure 5:
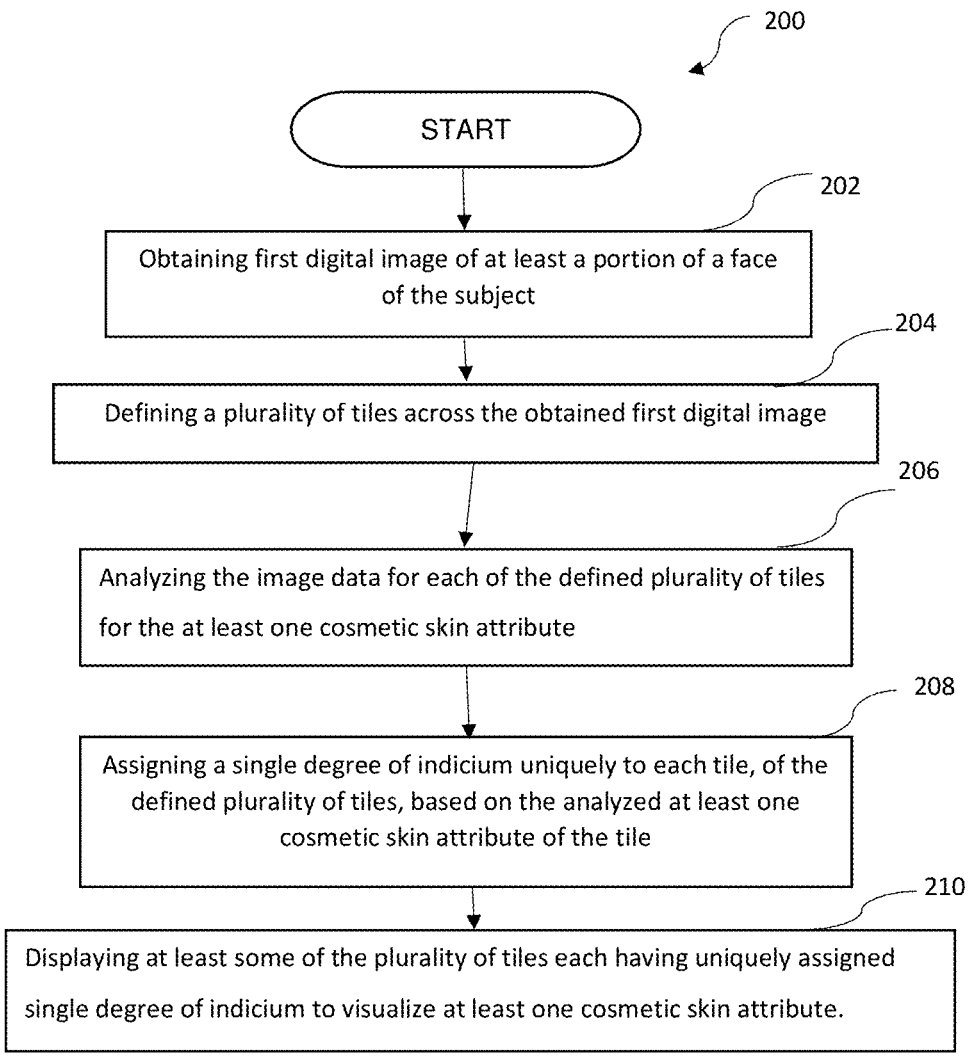
FIG. 5 is a flow chart illustrating a method of visualizing a cosmetic skin attribute according to the present invention.

Referring to FIGS. 4A and 5, when the processor 14b is initiated, the processor 14b causes a first digital image 51 of at least a portion of a face of the subject to be obtained, e.g. via image obtaining logic 144a in step 202. The processor 14b defines a plurality of tiles 54 across the obtained image data 20 (step 204). The plurality of tiles 54 may be adjacent so as to define a tile map 55 as shown in FIG. 4B. In step 206, the processor analyzes image data for each of the image data for each of the defined plurality of tiles 54 for the at least one cosmetic skin attribute. In step 208, a single degree of indicium 40 is assigned uniquely to each tile 54 of the defined plurality of tiles based on the analyzed at least one cosmetic skin attribute. At least some of the plurality of tiles, each having uniquely assigned single degree of indicium are displayed in step 210 to visualize at least one cosmetic skin attribute as shown in FIG. 4C. By analyzing image data of an input digital image provided by an user (consumer), organizing and displaying the analyzed image data for each of the defined plurality of tiles in a single screen shot, the method 200 according to the present invention allow user/consumers to easily identify the cosmetic skin attributes while avoiding a burdensome task of navigating through user interfaces displaying information in separate windows under different lighting systems required to visualize cosmetic skin attributes. For example, specific conditions such as UV light may be required to visualize UV spots which are not perceivable by the unaided eye.

In an exemplary embodiment, a second digital image with uniquely assigned single degree of indicium for each tile may be interposed the first digital image 51. It will be appreciated that a size of the tile 54 may be defined by a number of pixels on a horizontal side (tile width, W) and a number of pixels on a vertical side (tile height, H). In an exemplary method according to the present invention, each tile may comprise a tile size of not greater than 100 by 100 pixels, from 1 by 1 pixels to 100 by 100 pixels, from 2 by 2 pixels to 100 by 100 pixels, from 5 by 5 pixels to 90 pixels by 90 pixels, from 40 by 40 pixels to 70 by 70 pixels or different combinations of the upper and lower limits described above or combinations of any integer in the ranges listed above. A technical effect of having the tile size in the above ranges is that it enables a shorter processing time for analysis of the image data, and accordingly enable a display to visualize at least one cosmetic skin attribute in a shorter amount of time.

Referring to FIG. 1, the network 100 may be used to acquire digital images from the portable electronic device 12 and transmitting the digital images to the apparatus 14 to be used in the method 200 according to the present invention. An input device 12a may be coupled to or integral with the portable electronic device 12 for receiving a user input for initiating the processor 14b. The portable electronic device 12 may comprise an output device 12b for displaying the plurality of tiles, each having uniquely assigned single degree of indicium. The input device 12a may include but is not limited to a mouse, a touch screen display, or the like. The output device 12b may include but is not limited to a touch screen display, a non-touch screen display, a printer, a projector for projecting the facial image map 30 on a display surface such as for example a mirror as described hereinafter with respect to FIG. 2.

Figure 2:
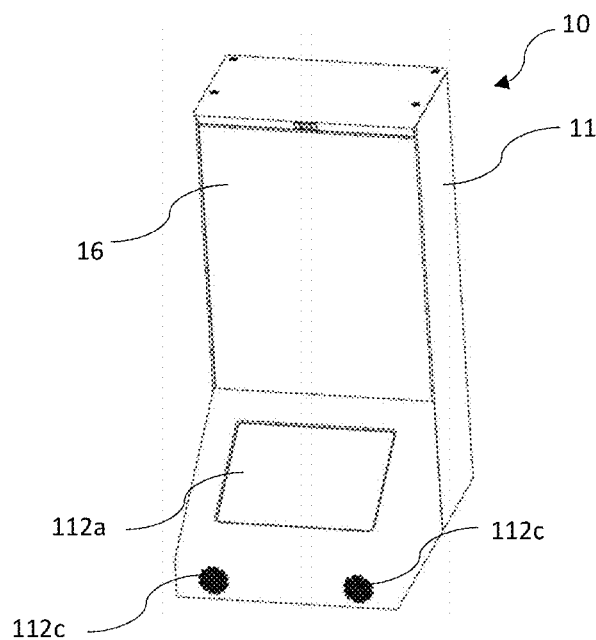
FIG. 2 is a diagram illustrating an alternative exemplary system for visualizing a cosmetic skin attribute according to the present invention.
Figure 3:
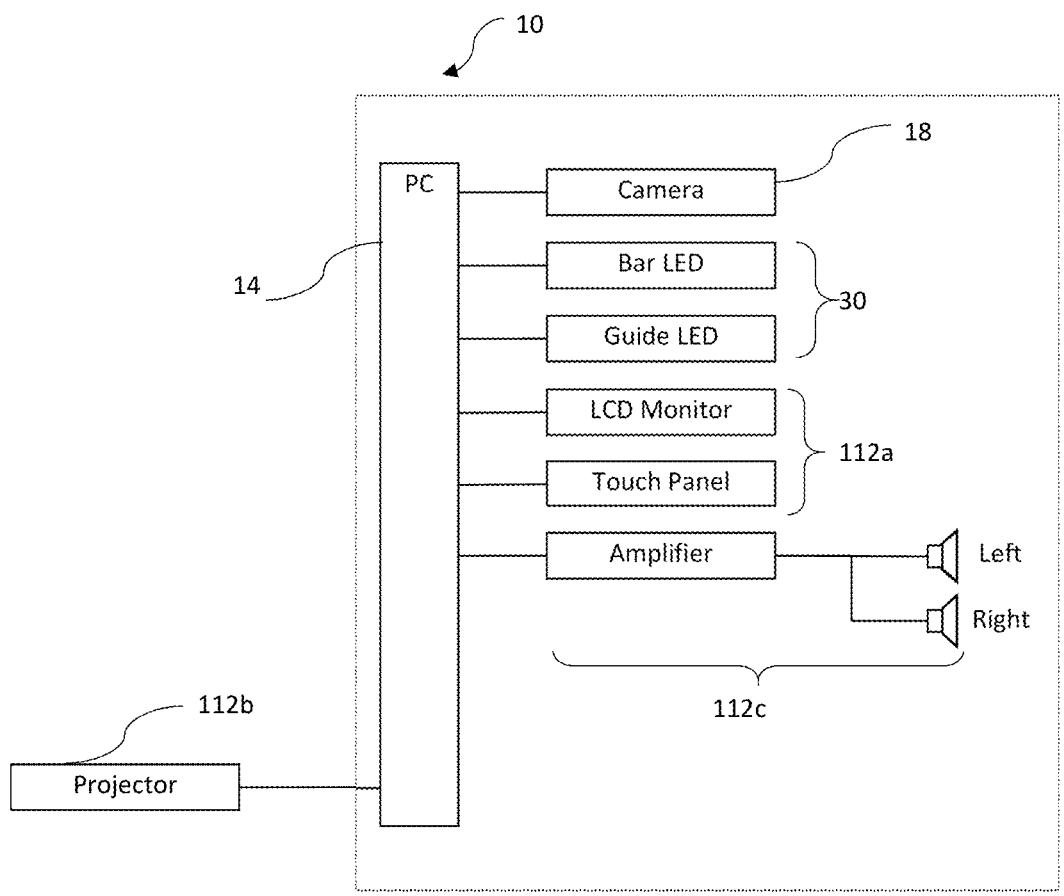
FIG. 3 is a block diagram illustrating components of an exemplary system for visualizing a cosmetic skin attribute according to the present invention.

FIG. 2 is a perspective view of the system 10 configured as a stand-alone imaging system that is located at a retail cosmetics counter for the purpose of visualizing at least one cosmetic skin attribute and recommending cosmetic and skin care products based on the visualized at least one cosmetic skin attribute. FIG. 3 is a block diagram of the system 10 of FIG. 2. Referring to FIGS. 2 and 3, the system 10 comprises a housing 11 for the apparatus 14 of FIG. 1 connected to an image obtaining device 18 for acquiring a digital image of a subject for visualizing at least one cosmetic skin attribute. Referring to FIG. 2, the system 10 may comprise a mirror 16, and the image obtaining device 18 may be mounted behind the mirror 16 within the housing 11 so that the image obtaining device 18 may be hidden from view. The image obtaining device 18 may be a digital camera, an analog camera connected to a digitizing circuit, a scanner, a video camera or the like. The system 10 may include lights 30 such as LED lights arranged about the housing 11 to form an LED lighting system for assisting in generating a digital image of a subject. The system 10 has an input device 112a for receiving a user input. The system 10 may further comprise an output device 112b such as a projector configured to receive and project the facial map 30 for display on the mirror 16. The projector is not shown in FIG. 2 as it may be a peripheral component that is separate from the housing 11 but coupled to the apparatus 14 to form the system 10. The system 10 may further comprise a second output device 112c such as one or more speakers optionally coupled to an amplifier for generating audio guidance output to complement and/or enhance an overall consumer experience.

To explain the way the system 10 and the method 200 works to visualize at least one cosmetic skin attribute according to the present invention, it is helpful to understand how a digital image of a face of the subject is obtained in step 202, how the tiles are defined in step 204, how the image data is analyzed in step 206, how a single degree of indicium is assigned uniquely to each tile in step 208 and how the tiles are displayed in step 210. Accordingly, the steps 202, 204, 206, 208, 210 of the method 200 according to the present invention is described hereinafter as individual processes for performing each step. Each process may also be described as a sub-routine, i.e. a sequence of program instructions that performs a corresponding step according to the method 200 according to the present invention.

Obtaining Digital Image

Figures 6A, 6B, 6C:
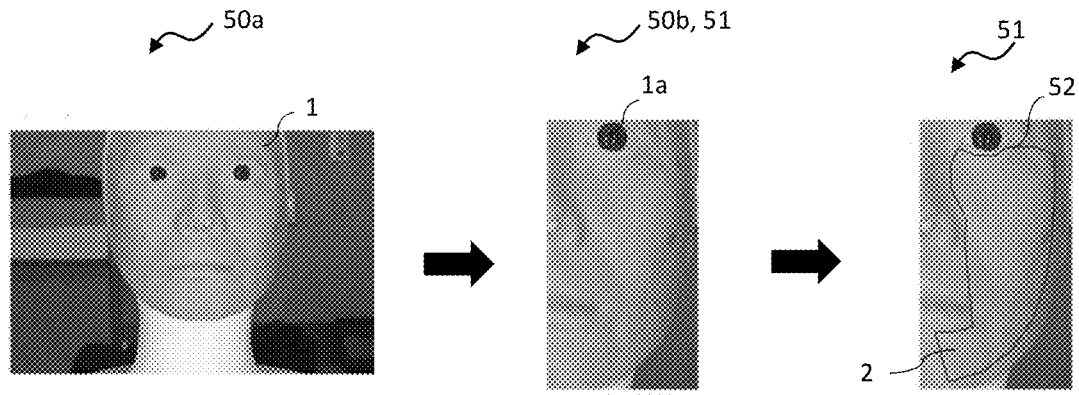
FIGS. 6A to 6C are a series of process flow diagrams illustrating details of a step of obtaining a first digital image in a method of visualizing a cosmetic skin attribute according to the present invention.
Figure 7:
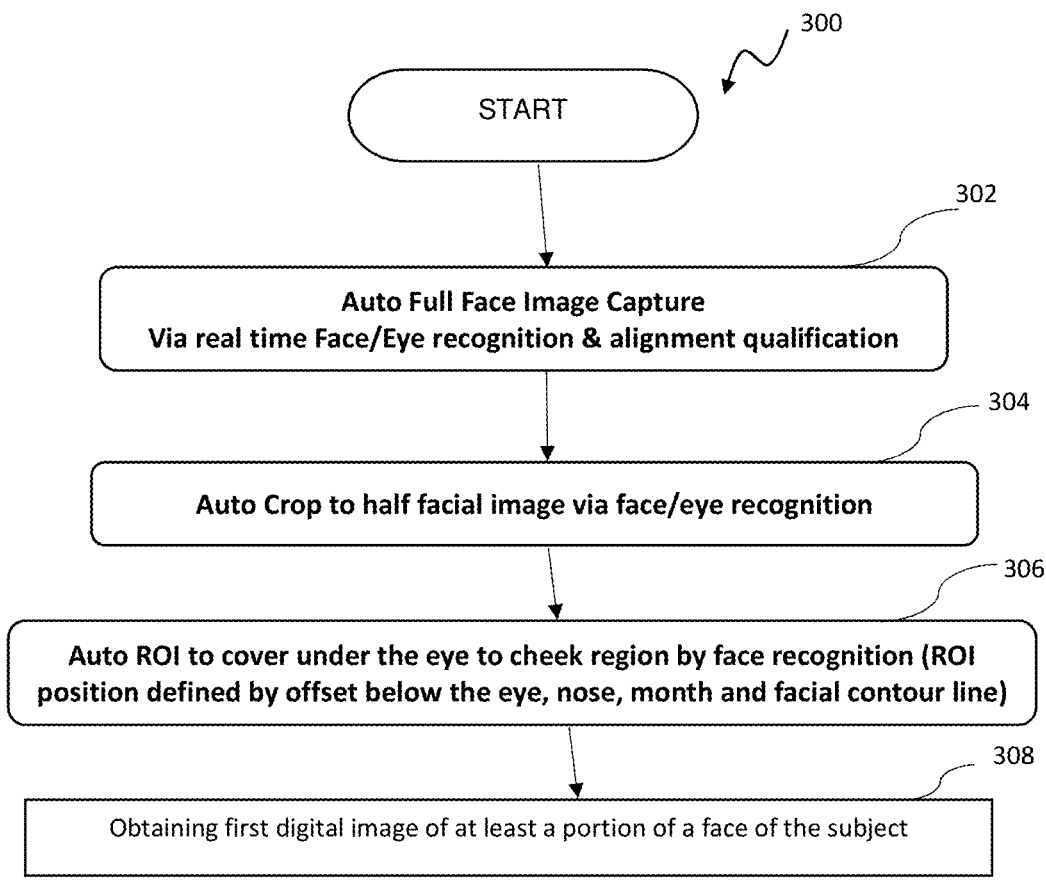
FIG. 7 is a flow chart illustrating the steps of obtaining the first digital image.

The step 202 of obtaining a digital image according to the method 200 according to the present invention is described with reference to FIGS. 6A, 6B and 6C which is a series of process flow diagrams illustrating how the first digital image is obtained, and FIG. 7 is a flow chart of a process 300 of obtaining digital image corresponding to the step 202.

An input image 50a of the face 1 is illustrated in FIG. 6A. The input image 50a may be captured by a user, for example, using the camera 18 in a step 302 of the process 300 as shown in FIG. 7. FIG. 6B illustrates a step 304 of cropping the input image 50a to obtain an edited image data 50b which comprises at least a portion of the face. The input image 50a may be cropped by identifying an anchor feature 1a of the face, including but not limited to facial features such as eyes, nose, nostrils, corners of the mouth or the like, and cropping accordingly. While the eye is depicted as the anchor feature 1a as shown in FIG. 6B, it will be appreciated that this is merely an example and any prominent or detectable facial feature(s) may be an anchor feature. The edited image data 50b may be a first digital image 51 that is obtained in step 308. Alternatively, as shown in FIG. 6C, the edited image data 50b may be further processed by cropping to remove one or more unwanted portions of the input image 50a thereby obtaining the first digital image 51 which includes the at least a portion of the face 1 defined by a boundary line 52 in step 308. The obtained first digital image 51 may comprise at least one region of interest (ROI) 2 of the at least a portion of the face 1 that is defined by the boundary line 52. The ROI 2 may be the entire portion of the face 1, preferably at least a portion of the face, more preferably, one or more skin regions that defines the at least portion of the face 1. Details of how the skin regions are defined are described hereinafter with reference to FIGS. 10A to 10C, and the flowchart of FIG. 11.

Optionally, the process 300 may comprise step 306 in which the ROI 2 may be selected from the group consisting of: a skin region around the eye ("eye region 2a"), a skin region around the cheek ("cheek region 2b"), a skin region around the mouth ("mouth region 2c"), and combinations thereof, preferably the ROI 2 is a part of the at least a portion of the face 1 of the subject, more preferably the obtained first digital image define a left or right side of the face 1. The ROI 2 may comprise an area of at least 5%, from 10% to 100%, from 25% to 90% of the obtained first digital image.

Defining Tiles

Figure 8:
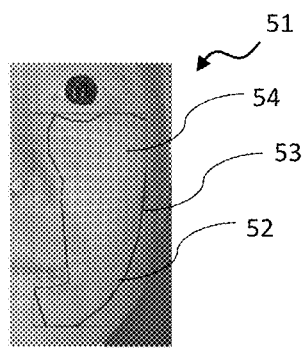
FIG. 8 is a picture illustrating a step of defining a plurality of tiles in a method of visualizing a cosmetic skin attribute according to the present invention.
Figure 9:
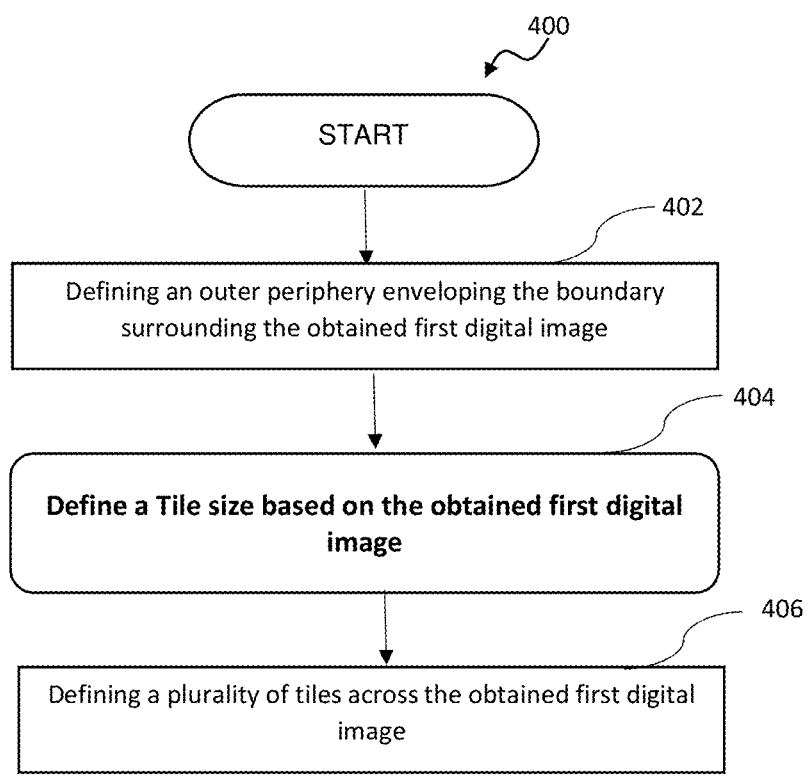
FIG. 9 is a flow chart illustrating the steps of defining the plurality of tiles.

FIG. 8 is a picture illustrating a plurality of tiles 54 on the first digital image data 51. FIG. 9 is a flow chart illustrating a process 400 of defining the plurality of tiles 54 on the first digital image data 51. Referring to FIG. 8, the first digital image data 51 includes the at least a portion of the face 1 defined by a boundary line 52 as described hereinbefore with reference to FIG. 6C. The process 400 comprises defining an outer periphery 53 enveloping the boundary line 52 surrounding the obtained first digital image (step 402). The obtained first digital image 51 is formed by a total number of pixels, for example, the obtained first digital image 51 may have a number of pixels which is determined at step 304 or step 306 depending an image size after cropping of the input image 50a. Accordingly, an overall image size based on the obtained first digital image 51 may be defined in step 404. For example, if the tile size is set at 40 by 40 pixels to 70 by 70 pixels, accordingly, the number of tiles 54 that form the plurality of the tiles 54 across the obtained first digital image 51 in step 406 will be obtained by dividing the overall image size by the specified tile size.

Analyzing Image Data

Figure 10:
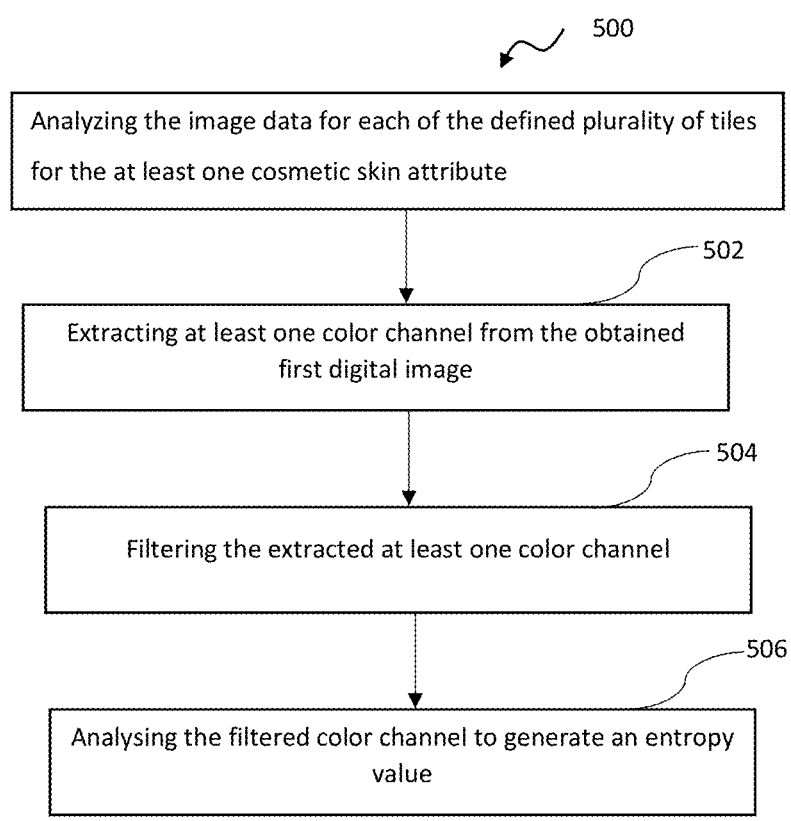
FIG. 10 is a flow chart illustrating a process 500 of analyzing the image data for each of the defined plurality of tiles according to the present invention.

FIG. 10 is a flow chart illustrating a process 500 of analyzing the image data for each of the defined plurality of tiles according to the present invention. The process 500 may begin in step 502 by extracting at least one color channel from the obtained first digital image to provide an extracted color channel image for analysis to obtain an entropy value for determining a cosmetic skin attribute. In the following description, the at least one color channel image is an image in the L*a*b* color system selected from the group consisting of a L color channel image, an a-channel image, a b-channel image, and a c-channel image from RGB color space, and combinations thereof; wherein the entropy value is selected from the group consisting of a L-entropy value, an a-entropy value, a b-entropy value, a c-entropy value, and combinations thereof; and wherein the function has the following formula:

Skin Attribute Index=$A+B\times(L$-entropy value)$+C\times(a$-entropy value)$+D\times(b$-entropy value)$+E\times(c$-entropy), wherein A, B, C, D, and E are constants; wherein at least one of B, C, D, and E is not 0.

However, it will be appreciated that the at least one color channel may also be a chromophore system and the at least one color channel may be a melanin channel or a hemoglobin channel. The color system may also be a HSL/HSV color system, and CMYK color system.

The extracted color channel may be filtered in step 504 and the filtered color channel is analyzed using entropy statistics to generate an entropy value for determining the at least one cosmetic skin attribute in step 506. It will be appreciated that the filtered color channel may also be analyzed using other descriptive statistics including but not limited to, standard deviation, mean, or the like. A technical effect of using entropy statistics is that it has a higher accuracy relative to the other descriptive statistics, and also enables a faster processing time of the method according to the present invention.

In step 506, the cosmetic skin attribute of the at least one portion of skin of the person is determined based on the entropy value.

The at least one color channel image may be an image in a color system selected from the group consisting of L*a*b* color system, RGB color system, HSL/HSV color system, and CMYK color system.

Table 1 below sets out each entropy value with a corresponding color channel image and corresponding cosmetic skin attributes to be determined based on the entropy value. The color channel image described in Table 1 is an image in the L*a*b* color system selected from the group consisting of a L channel image, an a-channel image, a b-channel image, a c-channel image, and combinations thereof.

TABLE 1

| Color Channel Image | Entropy Value | Cosmetic Skin Attribute |
|---|---|---|
| L channel image | L-entropy value | skin purity, skin tone, skin radiance |
| a-channel image | a-entropy value | skin inflammation |
| b-channel image | b-entropy value | skin pigmentation or skin dullness |
| c-channel image | c-entropy value | Skin topography, including but not limited to pores, wrinkles, fine lines, sagging, skin elasticity and combinations thereof. |

Determining the cosmetic skin attribute may comprise generating a Skin Attribute Index as a probability value indicative of a condition of the cosmetic skin attribute of the at least one portion of skin of the person relative to a defined population of people. Specifically, in a visual perception study, consumers may be asked to rank digital images (e.g. photographs) of the defined population of people for a cosmetic skin attribute based on a predetermined scale. The ranked digital images may be stored as a database so as to be analyzed according to the method 500 to determine an entropy value that has the highest correlation with the cosmetic skin attribute.

Alternatively, the Skin Attribute Index may be generated as a function of the entropy value defined by a function, F (Entropy Value), wherein said function is determined by a model established upon a training dataset. The training dataset may comprise: (i) a plurality of color channel images of a defined population of people, wherein each of the plurality of color channel images comprises facial skin of a person in the defined population of people, wherein the facial skin comprises the cosmetic skin attribute; (ii) an associated class definition based on the cosmetic skin attribute. Techniques for building training datasets are known to a person skilled in the field of image processing methods and will not be further described.

The model may be a regression model or a classification model, preferably a linear regression model, more preferably a machine learning linear regression model, most preferably a machine learning support vector regression (SVR) model. The SVR model is a specific example of a Support Vector Machine (SVM) model. A SVM model may also be a support vector classification model.

Using a SVR model enables the advantages of accuracy, reproducibility, speed in the performance of the method when implemented as a native application on a portable electronic device. In particular, the weight of a SVR model allows the native application to have a smaller hardware footprint, and consequently the methods according to the present invention may be easily deployed in portable electronic devices such as mobile phones with mobile phone operating systems (OS) including but not limited to iOS for the Apple™ phone or Android OS for Android phones.

The classification model may be used to classify consumers into a plurality of groups, each group having different degrees of a condition of the same cosmetic skin attribute, preferably two groups, more preferably three groups so as to define an associated class definition based on the numerical value of the Skin Attribute Index. For example, the method may display a heat map configured to classify regions of the skin into a high level of a cosmetic skin attribute condition or a low level of a cosmetic skin attribute condition based on thresholds assigned to each of the groups.

The at least one color channel image is an image in the L*a*b* color system selected from the group consisting of a L color channel image, an a-channel image, a b-channel image, and a c-channel image from RGB color system, and combinations thereof; wherein the entropy value is selected from the group consisting of a L-entropy value, an a-entropy value, a b-entropy value, a c-entropy value, and combinations thereof; and wherein the function has the following formula:

Skin Attribute Index=$A+B\times(L\text{-entropy value})+C\times(a\text{-entropy value})+D\times(b\text{-entropy value})+E\times(c\text{-entropy})$, wherein A, B, C, D, and E are constants; wherein at least one of B, C, D, and E is not 0.

It will be appreciated that the constants A, B, C, D, and E may vary based on the size and content of the training dataset, and may be any numerical value generated by the model based on the training dataset.

Specifically, each one of the entropy values above may be used alone or in combination with another one of the entropy values. For example using a single entropy value may result in faster computing speed which enables small devices with very basic hardware to be used, thereby resulting in a more efficient and cost effective product.

The at least one color channel image may be a L channel image; wherein the entropy value is a L-entropy value; wherein C, D, E each has a value of 0; and wherein the generated Skin Attribute Index is indicative of skin purity, skin tone or skin radiance.

It has been surprisingly found that a L-entropy value of a L color channel image has the highest correlation to skin purity.

A technical effect of selecting L-channel image as the at least one color channel image for a analyzing step to obtain a L-entropy value and to determine skin purity based on the L-entropy value according to methods according to the present invention is because L-entropy value has the highest correlation ($r=0.89$) to skin purity relative to other entropy values based on analyzing the color channel images. Below is data generated based on correlation with results from a visual perception study using statistical analysis using Pearson correlation coefficient (r). The correlation results are shown below in Table 2 below.

TABLE 2

| Entropy Value | Pearson Correlation Coefficient (r) with results of Visual Perception Study |
|---|---|
| L-entropy value | 0.89 |
| a-entropy value | 0.55 |
| b-entropy value | 0.7 |
| c-entropy value | 0.76 |

A higher Pearson correlation coefficient (r) means that the entropy value is a factor that contributes more to the condition of the cosmetic skin attribute that is studied in the visual perception study. Specifically, the visual perception study is conducted based on a predetermined number of panelists=302, age of the panelists=20-50. The panelists are asked rank photographs of people for skin purity (as an example of the cosmetic skin attribute) on a scale of 1 to 5. Based on the visual perception study results and above correlation results, it has been found that L channel entropy value of the filtered image (by frequency filter) has the highest correlation with the skin purity attribute. Therefore, use of the L-entropy value of the L channel to determine skin purity of at least a portion of skin of a person in a digital image can be used to transform skin purity from a visually imperceivable cosmetic skin attribute into an explainable cosmetic skin attribute in a consumer relevant way to consumers.

The at least one color channel image may be an a-channel image; wherein the entropy value is an a-entropy value; wherein B, D, E each has a value of 0; and wherein the generated Skin Attribute Index is indicative of skin inflammation.

The at least one color channel image may be a b-channel image; wherein the entropy value is a b-entropy value; wherein B, C, E each has a value of 0; and wherein the generated Skin Attribute Index is indicative of skin pigmentation or skin dullness.

The at least one color channel image may be a c-channel image; wherein the entropy value is a c-entropy value; wherein B, C, D each has a value of 0; and wherein the generated Skin Attribute Index is indicative of skin topography, which is preferably selected from the group consisting of: pores, fine lines, wrinkles, sagging, skin elasticity, and combinations thereof.

Preferably, the age of the subject and the average age of the defined population of people may be each independently from 18 to 60 years, preferably from 20 to 40 years, more preferably 25 to 35 years, even more preferably 28 to 32 years.

Optionally, filtering the extracted color channel image of step may comprise using a frequency filter, preferably the frequency filter is selected from the group consisting of: Difference of Gaussian (DoG) filter, Fast Fourier Transform (FFT) filter, Wavelet transformation filter, and combinations thereof; more preferably, the filter is a DoG filter. Optionally, the method 200 may further comprise applying an image correction factor to the filtered color channel prior to analyzing the filtered color channel.

Referring to FIG. 10, analyzing the image data may comprise analyzing at least two color channels, more preferably three color channels. In particular, the red color channel, the yellow color channel and the blue color channel may be described as follows. When the red color channel is in the L*a*b* color space, a-entropy is an entropy value of the filtered red color channel. When the yellow color channel is in the L*a*b* color system, b-entropy is an entropy value of the filtered yellow color channel. When the blue color channel corresponds to a texture channel, c-entropy is an entropy value of the blue color channel.

Displaying

Figure 25:
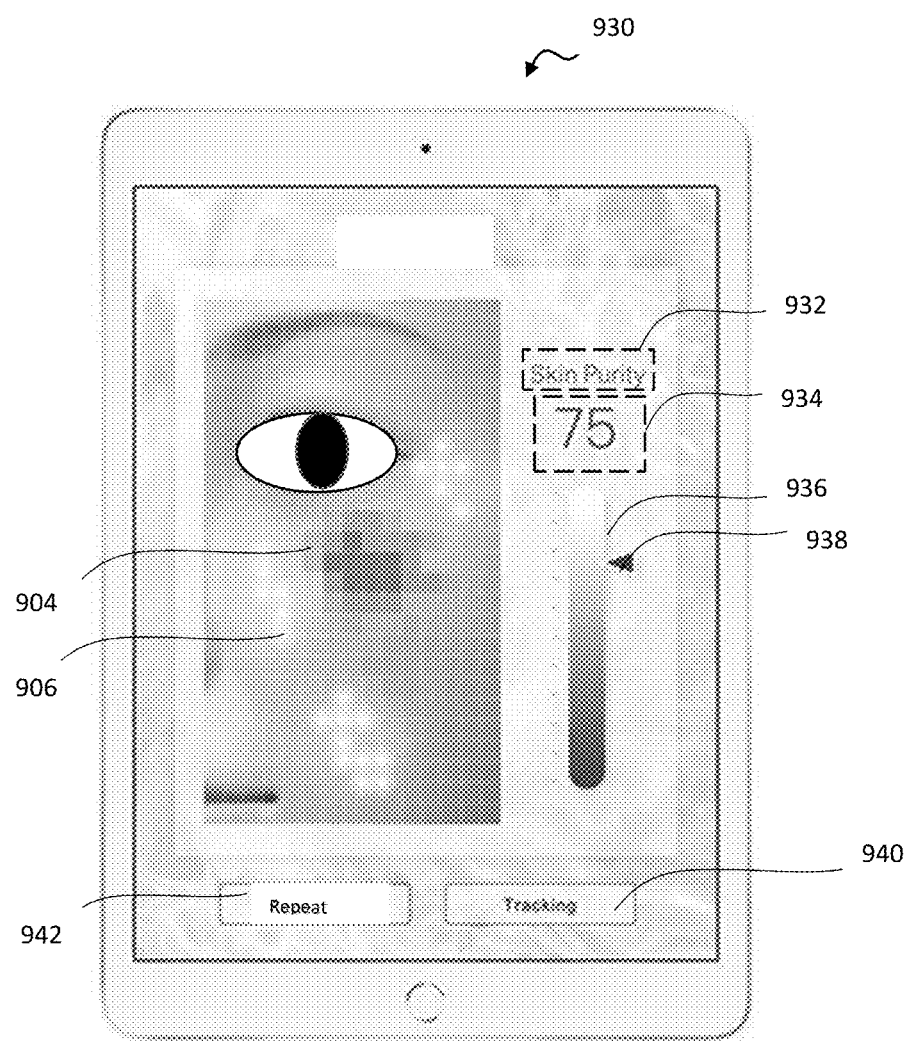
FIG. 25 is a screen shot illustrating an exemplary user interface for visualizing at least one cosmetic skin attribute according to the present invention.

The methods according to the present invention may further comprise a step of generating an image description corresponding to the generated Skin Attribute Index described hereinbefore for visualizing a cosmetic skin condition. The image description may comprise a heat map (such as shown in FIG. 16D, FIG. 25), an aggregate score indicative of a cosmetic skin attribute condition, such as a cosmetic skin attribute, skin age shown in the fourth area 194 in FIG. 16D, skin purity score shown in feature 934 in FIG. 25. The aggregate score may be computed based on the generated Skin Attribute Index described hereinbefore.

Figures 11A, 11B, 11C:
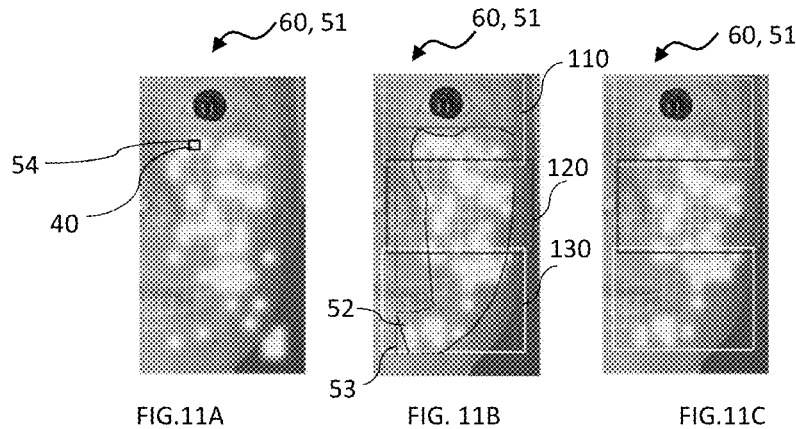
FIGS. 11A to 11C are process flow diagrams illustrating a process of displaying the plurality of tiles according to the present invention.
Figure 12:
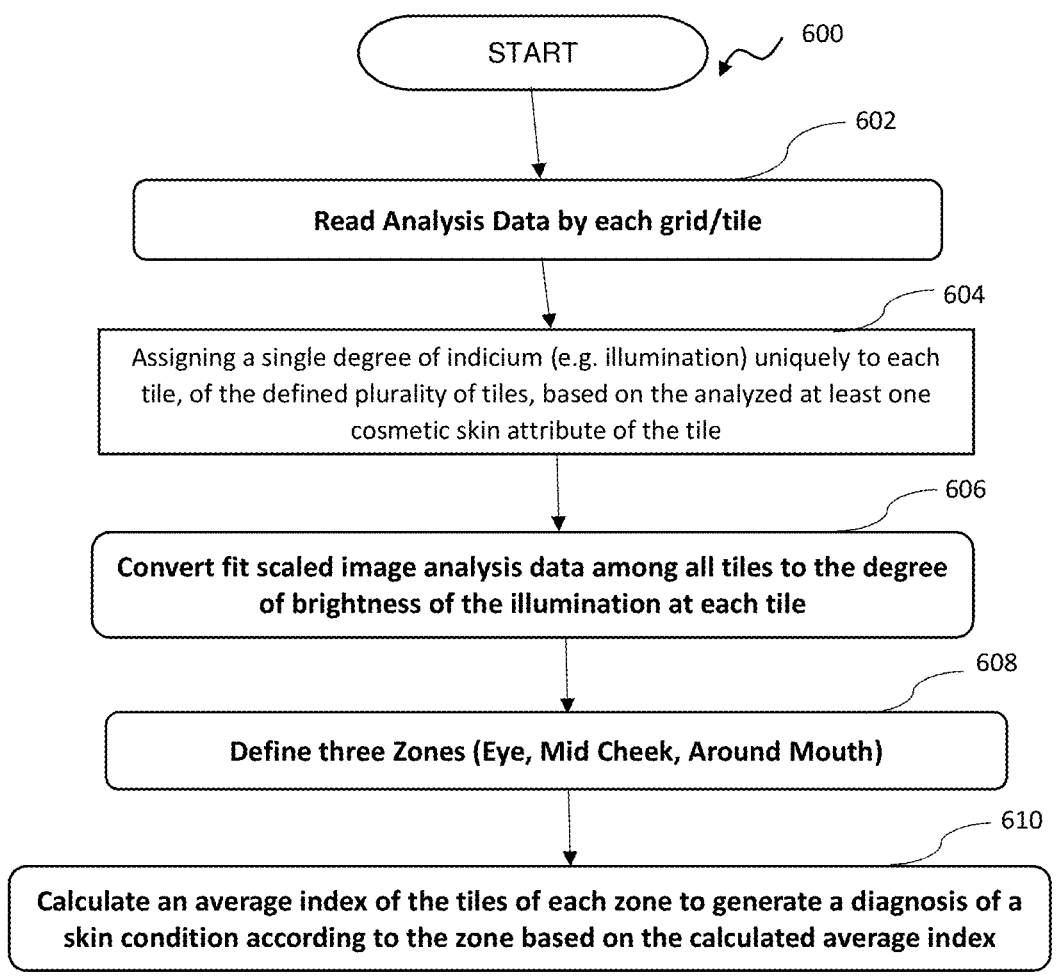
FIG. 12 is a flow chart illustrating a process of displaying the plurality of tiles according to the present invention.

FIGS. 11A to 11C are process flow diagrams illustrating details of a process of displaying a plurality of tiles according to the method of the present invention. FIG. 12 is a flow chart illustrating a process of displaying the plurality of tiles. FIG. 11A is a picture illustrating a second digital image 60 interposed on the first digital image 51. The second digital image 60 includes at least a portion of the face of the subject with displayed plurality of tiles 54 each having uniquely assigned single degree of indicium 40. FIG. 11B illustrates three zones, a first zone 110, a second zone 120, a third zone 130 displayed on the obtained first digital image based on the plurality of tiles 54 each having uniquely assigned single degree of indicium. Each zone 110, 120, 130 identifies a respective region of interest (ROI) 2 on the face 1 of the subject described hereinbefore with reference to FIGS. 6A to 6C and FIG. 7. FIG. 11C differs from FIG. 11B in that a boundary line 52 and an outer periphery 53 is displayed in the second digital image 60 of FIG. 11B but are not displayed in the second digital image 60 of FIG. 11C. The first zone 110 may comprise a first zone line having a first zone color 110a, the second zone 120 may comprise a second zone line having a second zone color 120a and the third zone 130 may comprise a third zone line having a third zone color 130a. Based on the analyzed image data of the tiles 54 in each zone, a color of each zone lines may be different to better visually distinguish the tiles that visualize cosmetic skin attributes which may be in a normal, beautiful, or vulnerable condition relative to the other zones of the subject, such as for example as illustrated in an exemplary user interface of FIG. 16D.

FIG. 12 is a flow chart illustrating a process 600 of displaying the plurality of tiles according to the present invention. The process 600 may begin in step 602 in which the processor reads analyzed image data of each tile 54 and assigns a single degree of indicium uniquely to each tile 54 of the plurality of tiles based on the analyzed at least one visually cosmetic skin attribute of the tile 54 (step 604). When the single degree of indicium is illumination, the analyzed image data of each of the tiles may be converted to reflect a corresponding degree of brightness of the illumination at each tile in step 606. In an exemplary example, the zone 110 may have a lower degree of illumination at each of the tiles within the zone 110 relative to a degree of illumination at each of the tiles within the zone 120. Further, in step 608, the zones may be defined such that the first zone 110 may correspond to an eye zone, the second zone 120 may correspond to a cheek zone and the third zone 130 corresponds to a mouth zone. An average index of the tiles of each zone may be calculated to generate a diagnosis of a skin condition correlating to a displayed cosmetic skin attribute according to the respective zone so as to assign a product recommendation item to the zone for treating the displayed cosmetic skin attribute in the zone. Specifically, the method 200 may further comprise displaying at least one product recommendation item to treat the displayed cosmetic skin attribute.

Figure 13A:
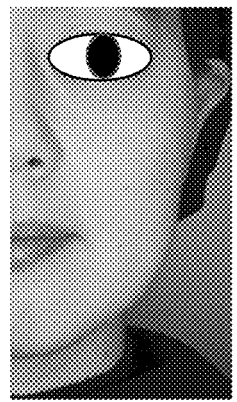
FIGS. 13A to 13D are process flow diagrams illustrating a method of visualizing at least one cosmetic skin attribute according to the present invention.
Figure 13B:
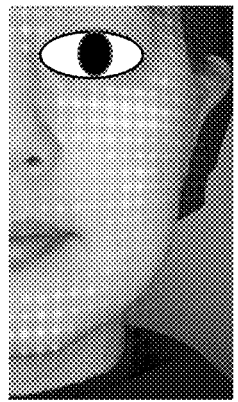
Figure 13C:
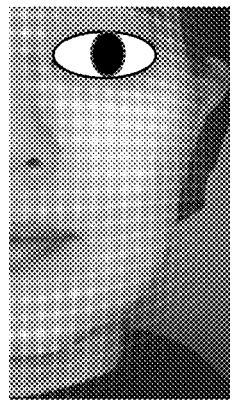
Figure 13D:
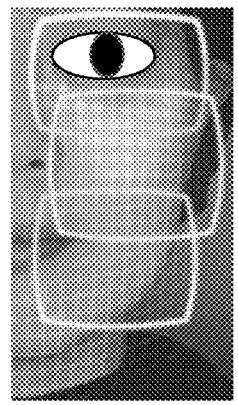
Figure 14:
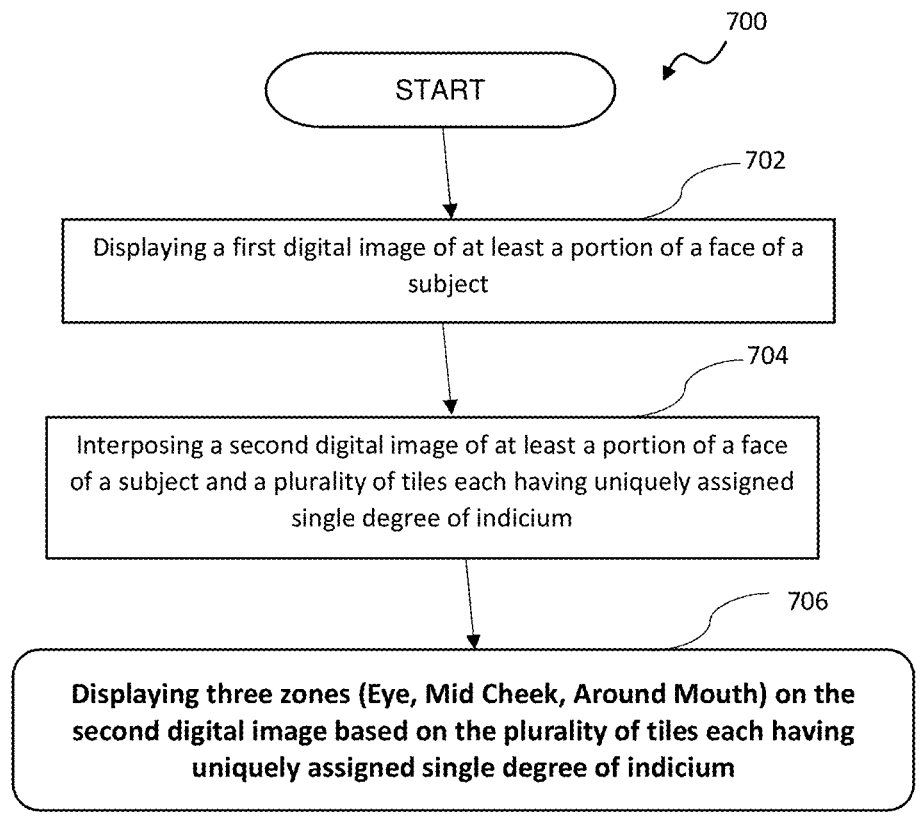
FIG. 14 is a flow chart illustrating a method of visualizing at least one cosmetic skin attribute according to the present invention.

FIGS. 13A to 13D are process flow diagrams illustrating a method of visualizing at least one cosmetic skin attribute according to the present invention. FIG. 14 is a flow chart illustrating a method 700 of visualizing at least one cosmetic skin attribute according to the present invention. FIG. 13A is a color picture illustrating a first digital image of at least a portion of a face of a subject that is displayed in step 702 of the method 700 of FIG. 14. FIG. 13B is a color picture illustrating a second digital image of at least a portion of a face of a subject and a plurality of tiles each having uniquely assigned single degree of indicium, wherein the second digital image is interposed on the first digital image in step 704. Optionally, the first digital image may be converted into grey scale as shown in FIG. 13C to provide better contrast between the plurality of tiles each having uniquely assigned single degree of indicium and the first digital image. In step 706, three zones are displayed on the second digital image based on the plurality of tiles each having uniquely assigned single degree of indicium.

Figure 15:
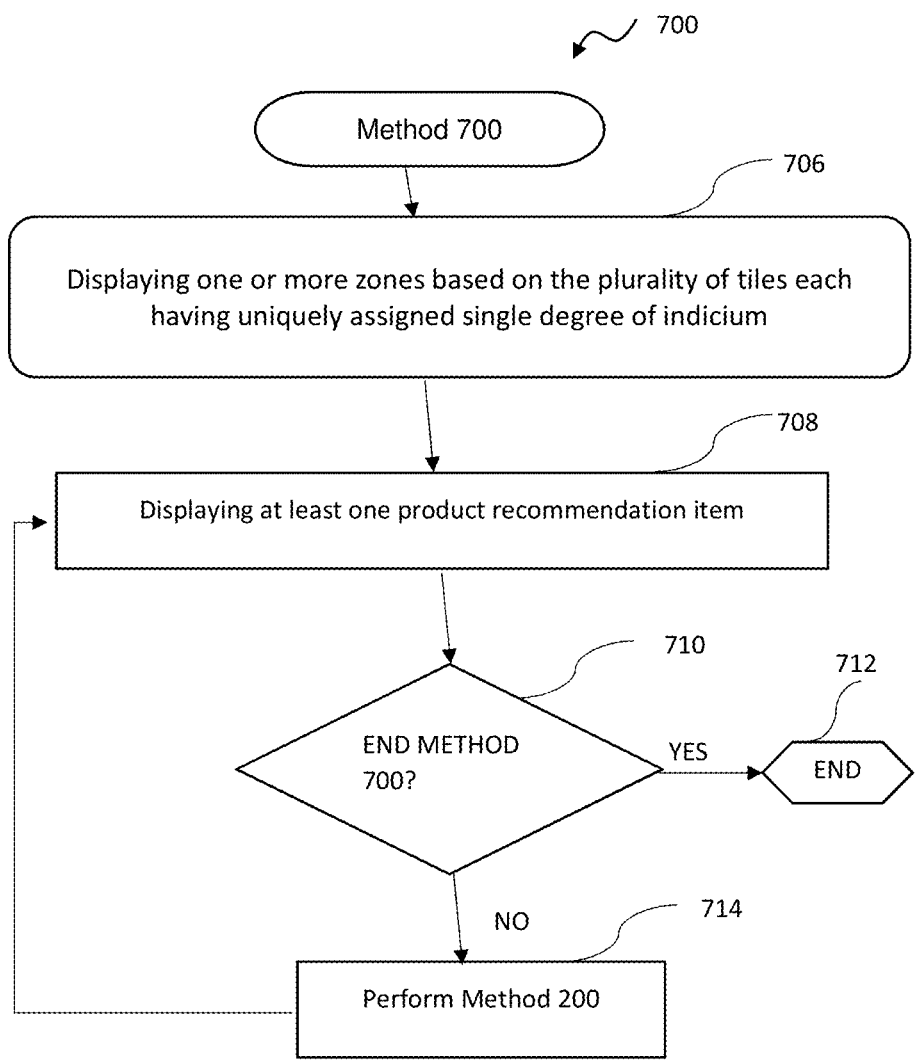
FIG. 15 is a flow chart illustrating an alternate method of visualizing at least one cosmetic skin attribute according to the present invention.

FIG. 15 is a flow chart illustrating a variation of the method 700 of visualizing at least one cosmetic skin attribute as illustrated in FIG. 14. At least one product recommendation item is displayed in step 708 following step 706 of the method 700 of FIG. 14. In step 710, the user is prompted to select to end the method 700 and the method 700 terminates in step 712 if the user selects YES. If the user selects NO, steps of the method 200 of FIG. 5 is performed and the method 700 returns to step 708.

Human Machine User Interface

The present invention also relates to a human machine user interface interface (hereinafter "user interface") for providing a product recommendation to treat at least one cosmetic skin attribute. The user interface may be a graphical user interface on a portable electronic apparatus including a touch screen display/display with an input device and an image obtaining device. The user interface may comprise a first area of the touch screen display displaying a first digital image of at least a portion of a face of the subject obtained from the image obtaining device and a second digital image interposed on the first digital image, the second digital image having the at least a portion of a face of the subject and said displayed plurality of tiles each having uniquely assigned single degree of indicium. The user interface may further comprise a second area of the touch screen display different from the first area, the second area displaying a selectable icon for receiving a user input, wherein an image of at least one product recommendation item to treat the displayed cosmetic skin attribute is displayed on the touch screen display if the user activates the selectable icon.

FIGS. 16A to 16E are screen shots, each illustrating an exemplary user interface cooperating with each other for visualizing a cosmetic skin attribute according to the present invention. Although FIGS. 16A to 16E are described as a series of user interfaces which are provided in a sequential manner in response to a preceding user interface, it will be appreciated that the user interfaces of FIGS. 16A to 16E may be programmed in multiple ways to define an overall user interface for visualizing at least one cosmetic skin attribute according to methods according to the present invention as described hereinbefore. Preferably, all the user interfaces of FIGS. 16A to 16E define an exemplary user interface for visualizing a cosmetic skin attribute according to the present invention.

Figure 16A:
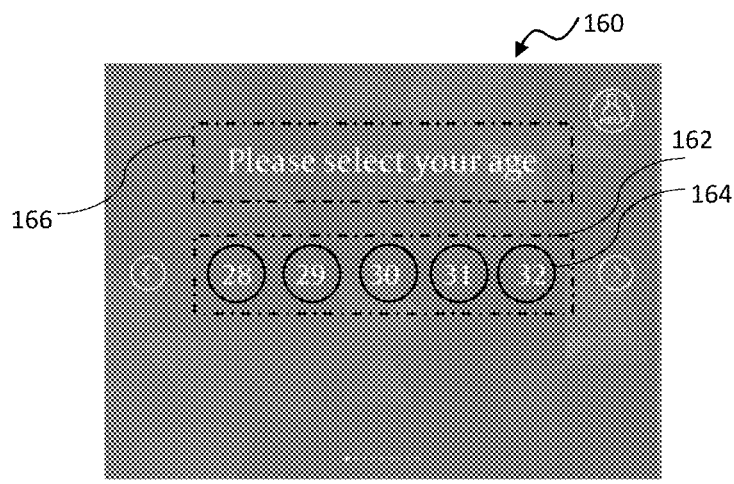
FIGS. 16A to 16E are screen shots, each illustrating an exemplary user interface for visualizing a cosmetic skin attribute according to the present invention.

FIG. 16A depicts a user interface 160 for receiving a first user input, preferably the first user input is the age of the user. The user interface 160 may comprise a first area 162 for receiving the first user input. The first area 162 may include one or more user input features 164 for receiving the first user input. The user input feature 164 may be such as for example, a selectable input icon corresponding to a predetermined user feature such as for example a user's age as shown in FIG. 16A. The user interface 160 may further comprise a second area 166 including corresponding instructions to the user for providing the first user input. The second area 166 may be disposed above the first area 162 so as to be provide a more user-friendly interface. The user interface 160 may be part of a start option for beginning a method 200 according to the present invention.

Figure 16B:
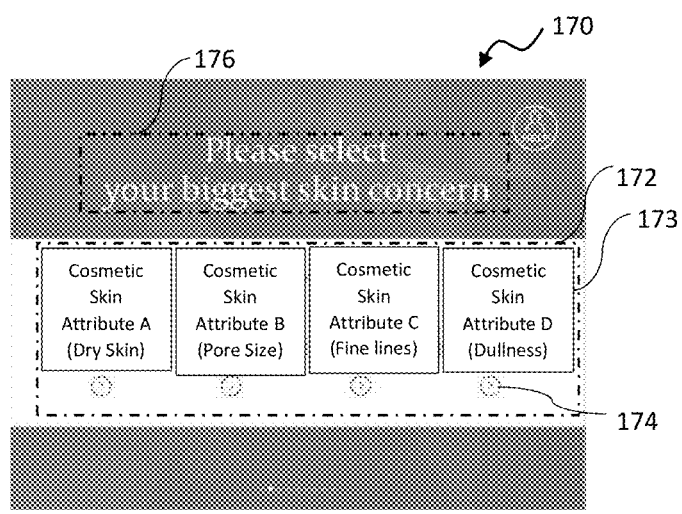

FIG. 16B depicts a user interface 170 for receiving a second user input, preferably the second user input is a cosmetic skin attribute that is causing concern to the user. The cosmetic skin attribute may be described as a skin concern of the user. The user interface 170 may be provided in response to the selection of a first user input from the user input feature 164 of FIG. 16A. The user interface 170 may comprise a first area 172 for receiving the second user input. The first area 172 may include one or more user input features 174 for receiving the second user input. The user input feature 174 may be such as for example, a selectable input icon corresponding to a predetermined skin concern. The first area 172 may further comprise an explanatory area 173 corresponding to the one or more input features 174 in which the explanatory area 173 includes a brief description of a cosmetic skin attribute or the skin concern. The user interface 170 may further comprise a second area 176 including corresponding instructions to the user for providing the user input. The second area 176 may be disposed above the first area 172 so as to be provide a more user-friendly interface.

Figure 16C:
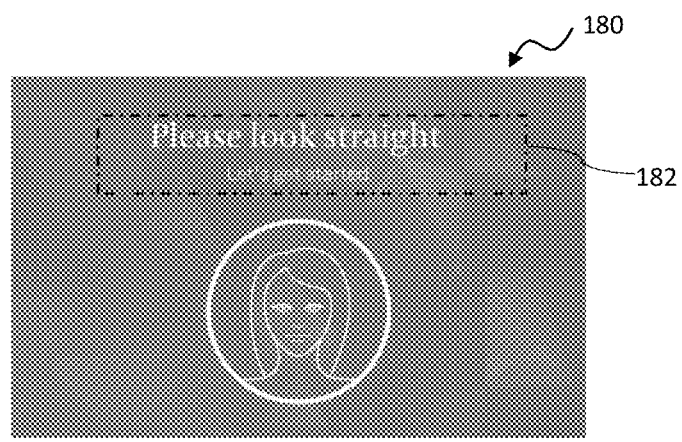
Figure 16D:
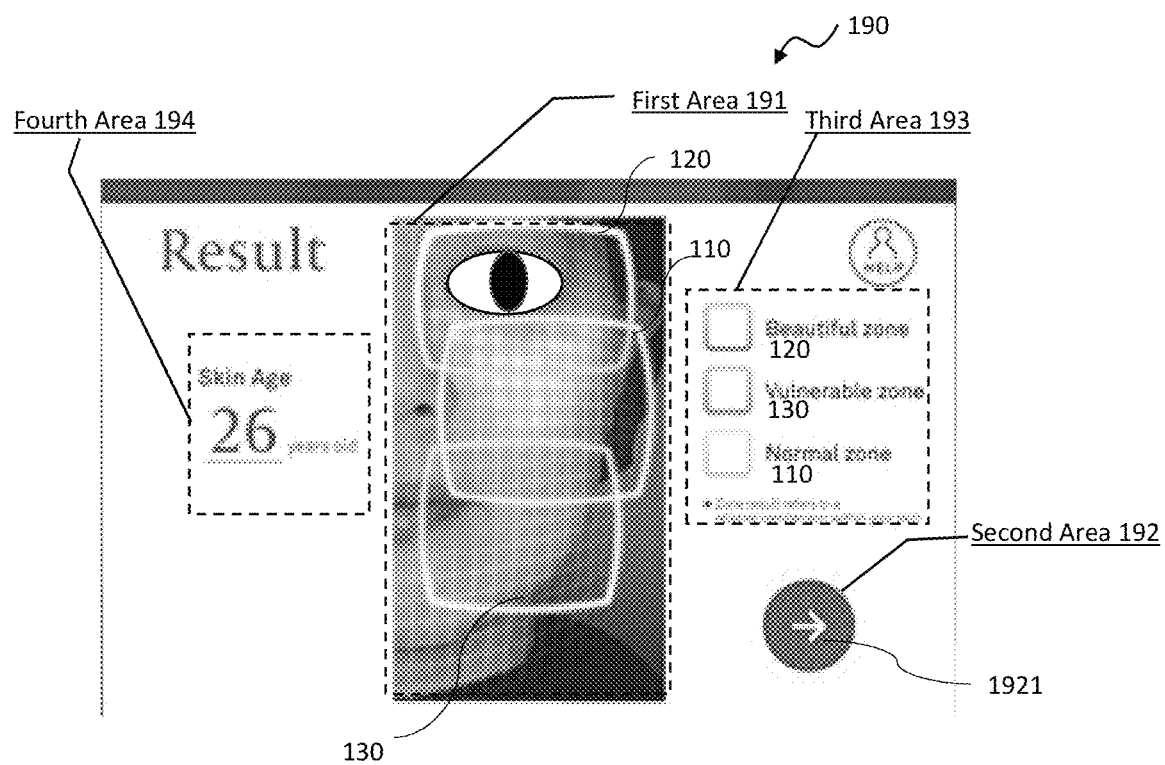

FIG. 16C depicts a user interface 180 for obtaining an input image of a user. The user interface 180 may comprise a first area 182 with instructions for aligning an anchor feature (such as eyes) so as to obtain the first digital image according to the process as described in FIG. 7. The user interface 180 may be provided in response to the selection of the second user input through the one or more user input features 174 of FIG. 16B.

FIG. 16D depicts a user interface 190 for displaying at least one cosmetic skin attribute. The user interface 190 may be provided after the input image of the user is obtained in the user interface 180 of FIG. 16C. The user interface 190 may comprise a first area 191 displaying the plurality of tiles each having uniquely assigned single degree of indicium to visualize at least one cosmetic skin attribute according to methods of the present invention. The first area 191 may display similar features as shown in FIG. 13D but differs only in that lines defining the plurality of tiles may be turned off and/or set as an invisible layer. The first area 191 may comprise a first zone 110 corresponding to an eye zone of the at least a portion of the face of the user, a second zone 120 corresponding to a cheek zone of the at least a portion of the face of the user, and a third zone 130 corresponding to a mouth zone of the at least a portion of the face of the user. As shown in FIG. 16D, a zone result may be displayed in a third area 193 whereby the zone result comprises an index which may be generated for each zone based on a relative comparison of the indexes of the zones within the at least a portion of the face of the user. In an exemplary embodiment, depending on the zone results, the first zone 110 may be described as a normal/beautiful/vulnerable zone, the second zone 120 may be described as a normal/beautiful/vulnerable zone and the third zone 130 may be described as a normal/beautiful/vulnerable zone. Preferably, each zone may have different descriptions based on the relative differences in the zone results. The user interface 190 also includes a second area 192 for receiving a third user input. The second area 192 may include one or more user input features 1921 for receiving the third user input. The user input feature 1921 may be such as for example, a selectable input icon for proceeding with a next step of the method according to the present invention. Optionally, the user interface 190 may comprise a fourth area 194 for displaying a skin age of the user based on the analyzed at least one cosmetic skin attribute of each tile of the plurality of tiles based on the obtained first digital image of the at least a portion of the face of the user.

Figure 16E:
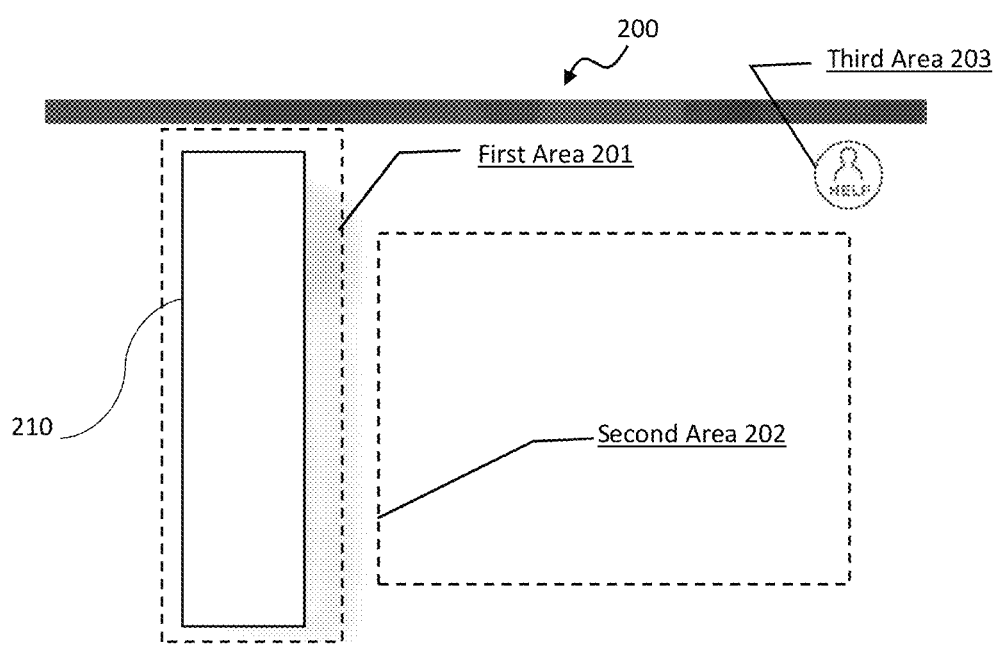

FIG. 16E depicts a user interface 200 comprising a first area 201 for displaying a product recommendation item 210. The user interface 200 may be provided in response to selection of the user input feature 1921 from the user interface 190 of FIG. 16D. Optionally, the user interface 200 may comprise a second area 202 for providing details of the product recommendation item 210. Preferably, the user interface 200 may comprise a third area 203 for receiving a fourth user input such as for example request for assistance from a product consultant for enquiry and/or purchase of the product recommendation item 210. The third area 203 may include one or more user input features 2031 for receiving the fourth user input. The user input feature 2031 may be such as for example, a selectable input icon for proceeding with a next step of the method according to the present invention.

Figure 17A:
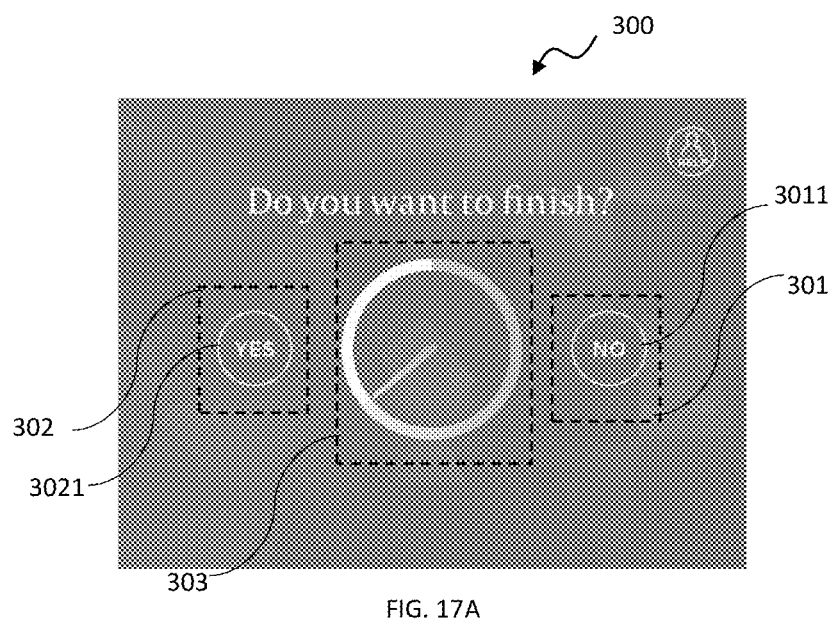
FIGS. 17A and 17B are screen shots, each illustrating an exemplary user interface for providing additional prompts for repeating a method for visualizing a cosmetic skin attribute according to the present invention.

FIG. 17A is a screen shot illustrating an exemplary user interface 300 for providing additional prompts according to step 710 of the method 700 for visualizing a cosmetic skin attribute according to the present invention as described with reference to FIG. 15. The user interface 300 may be provided in response to selection of the user input feature 1921 of FIG. 16D or generated automatically by the processor after the user interface 200 of FIG. 16E.

Figure 17B:
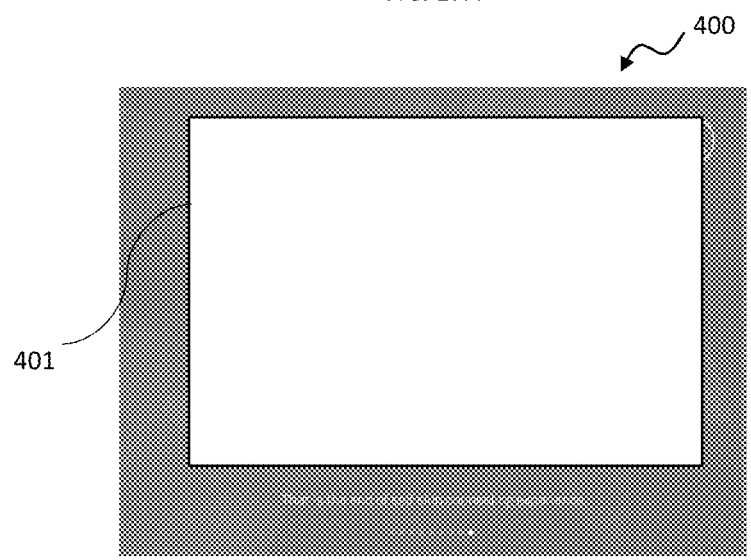

Referring to FIG. 17A, the user interface 300 may comprise a first area 301 for receiving a fifth user input such as for example to end the method according to step 712 of the method 700, and a second area 302 for receiving a sixth user input such as for example to continue a next step according to methods of the present invention. The first and second areas 301, 302 may include one or more user input features 3011, 3021 for receiving the fourth user input. The user input feature 3011, 3021 may be such as for example, a selectable input icon for proceeding with a next step of the method according to the present invention. Optionally, the user interface 300 may comprise a third area 303 including a timer feature for setting a time period for the user to provide the fifth or sixth user input. FIG. 17B is a screen shot illustrating an exemplary user interface 400 for displaying a step 712 of the method 700. The user interface 400 may comprise a first area 401 for illustrating content for confirming the end of the method 700 to the user.

Figure 18A:
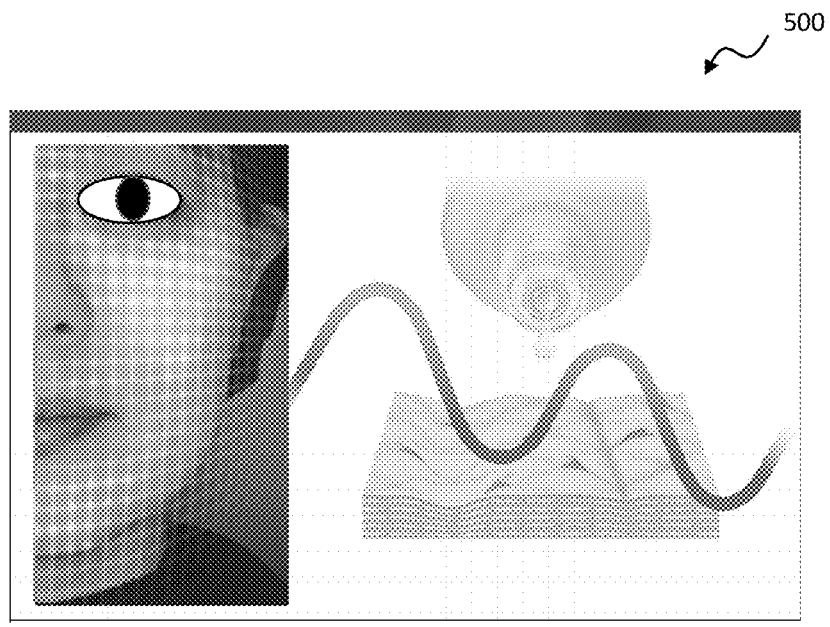
FIGS. 18A and 18B are screen shots, each illustrating an exemplary user interface for displaying details of a product recommendation for treating a cosmetic skin attribute according to the present invention.
Figure 18B:
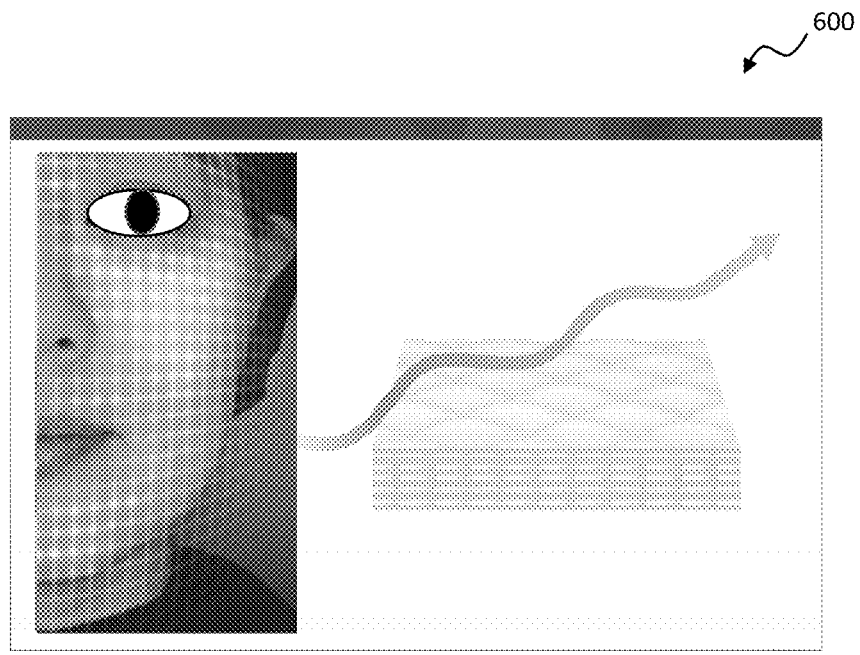

FIGS. 18A and 18B are screen shots, each illustrating an exemplary user interface 500, 600 for displaying details of a product recommendation item and how the product recommendation item works to treat a cosmetic skin attribute according to the present invention.

In an exemplary embodiment, the present invention may relate to a user interface for providing a product recommendation to treat at least one cosmetic skin attribute, the user interface being on a portable electronic apparatus including a display and an image obtaining device. The user interface may comprise a first area of the display displaying a first digital image of at least a portion of a face of the subject obtained from the image obtaining device and a second digital image interposed on the first digital image, the second digital image having the at least a portion of a face of the subject and said displayed plurality of tiles each having uniquely assigned single degree of indicium; a second area of the display different from the first area, the second area displaying a voice input component for receiving an user input, wherein an image of at least one product recommendation item to treat the displayed cosmetic skin attribute is displayed on the touch screen display if the user activates the voice input component; and a third area of the display different from the first area, the third area displaying the image of at least one product recommendation item to treat the displayed cosmetic skin attribute.

Figure 19:
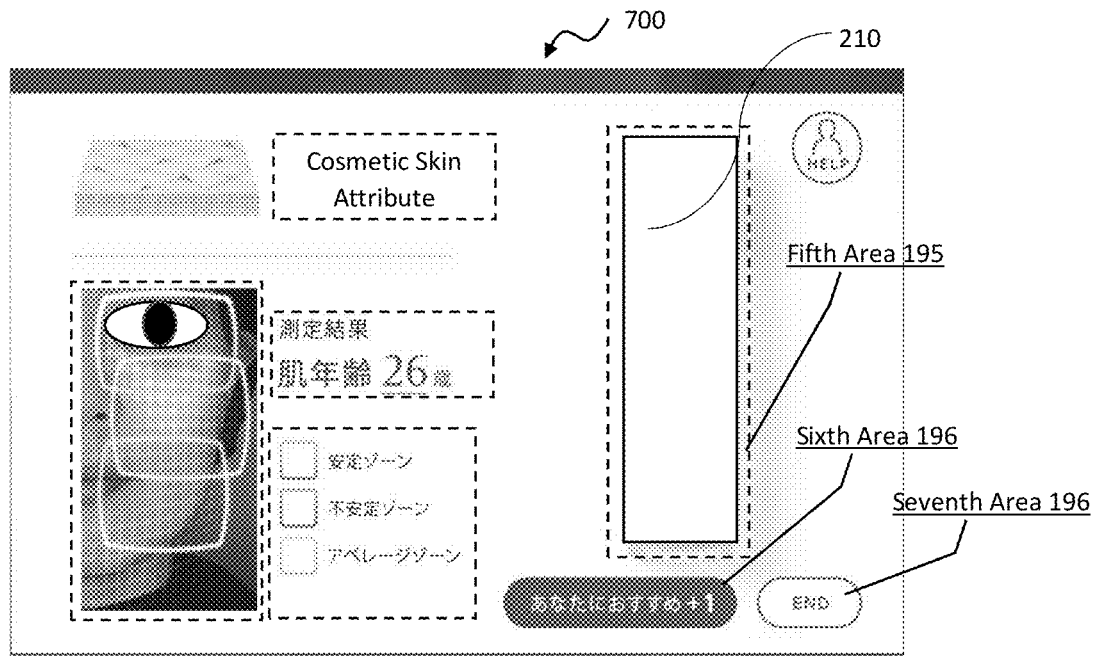
FIG. 19 is a variation of a screen shot of an exemplary user interface of FIG. 16D for displaying a cosmetic skin attribute according to the present invention.

FIG. 19 is a screen shot illustrating a variation of an exemplary user interface 700 of FIG. 16D for displaying a cosmetic skin attribute according to the present invention. Specifically, the user interface 700 of FIG. 19 has substantially the same features as the user interface 190 of FIG. 16D and differs in the following additional features including a fifth area 195 for displaying at least one product recommendation item 210, a sixth area 196 for receiving a user input such as for example to continue a next step according to methods of the present invention such as for example to add a further product recommendation item, and a seventh area 197 for receiving a user input such as for example to terminate the methods of the present invention. The fifth and sixth areas 195, 196 may include one or more user input features for receiving the respective user input. The user input feature may be such as for example, a selectable input icon for proceeding with a next step of the method according to the present invention.

Figure 20:
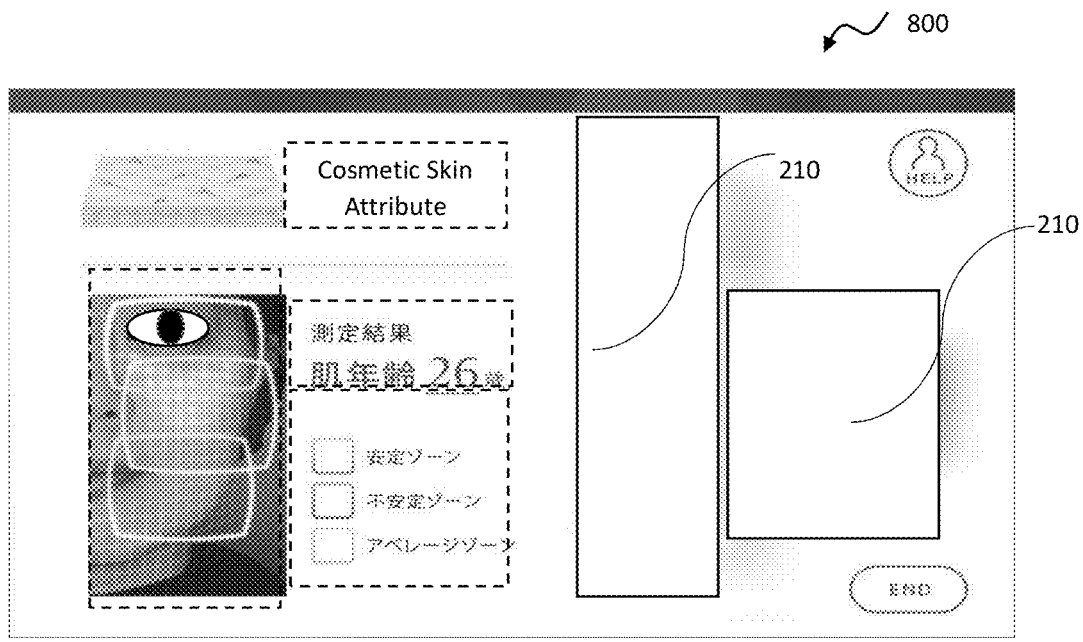
FIG. 20 is a screen shot illustrating an exemplary user interface for displaying details of a product recommendation for treating a cosmetic skin attribute according to the present invention.

FIG. 20 is a screen shot illustrating an exemplary user interface 800 for displaying one or more product recommendation items according to the present invention. The user interface 800 may be provided in response to selecting the user input feature in the sixth area 196. The user interface 800 has substantially the same features as the user interface 700 and differs in that the user interface 800 displays a plurality of product recommendation items 210.

The method according to the present invention may comprise displaying at least one region of interest (ROI), preferably one to three ROI, more preferably three ROI based on the plurality of tiles each having uniquely assigned single degree of indicium; preferably the displayed one of the three ROI displays a cosmetic skin attribute condition that is better relative to a cosmetic skin attribute condition of other ones of the three ROI based on the analyzed at least one cosmetic skin attribute of the tile.

Figure 21:
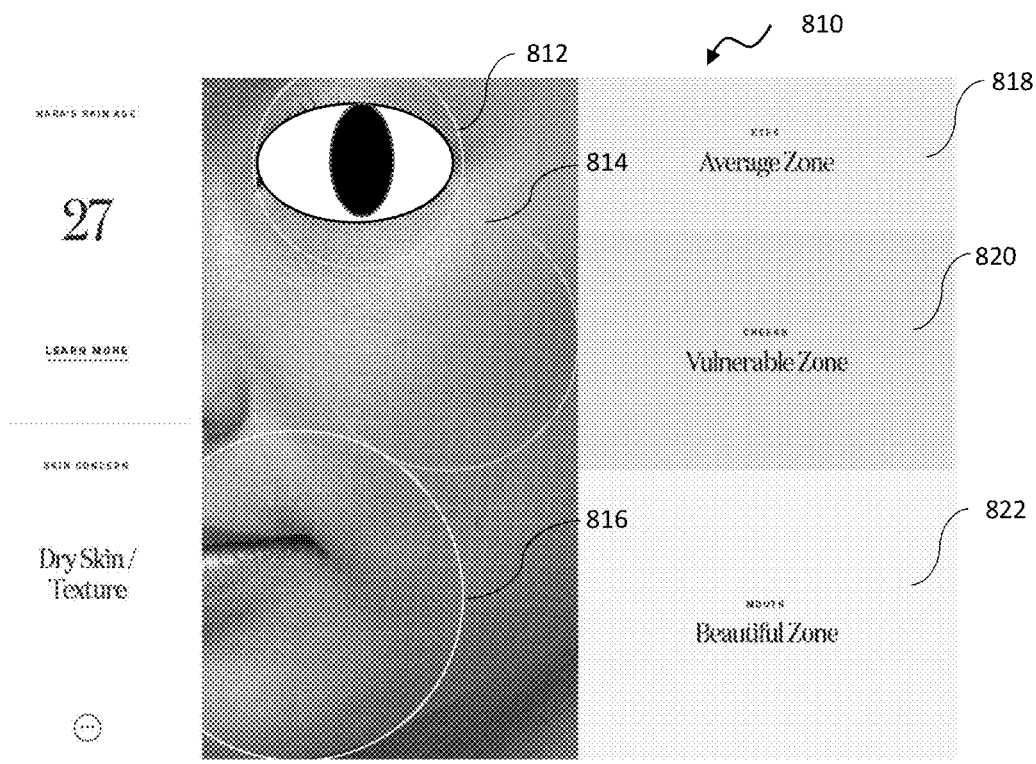
FIG. 21 is an exemplary user interface for visualizing a cosmetic skin attribute according to the present invention.

FIG. 21 is a screen shot of an exemplary user interface 810 for displaying a cosmetic skin attribute. Specifically, the user interface 810 has substantially the same features as the user interface of 16D and differs in that the plurality of tiles are not displayed. Specifically, the user interface 810 comprise three ROI each having a boundary line defining the respective ROI. Specifically, the three ROI comprise a first ROI 812 defining an eye region, a second ROI 814 defining a cheek region and a third ROI 816 defining a mouth region. The cosmetic skin attribute is dry skin/texture and accordingly an image description 818, 820, 822 explaining a condition of the cosmetic skin attribute is disposed next to each of the three ROI 812, 814, 816. For example, the third ROI 816 may have an image description 822 indicating that the third ROI 816 is a beautiful zone on the face based on the analyzed cosmetic skin attribute of the tile which is not displayed.

Figure 22:
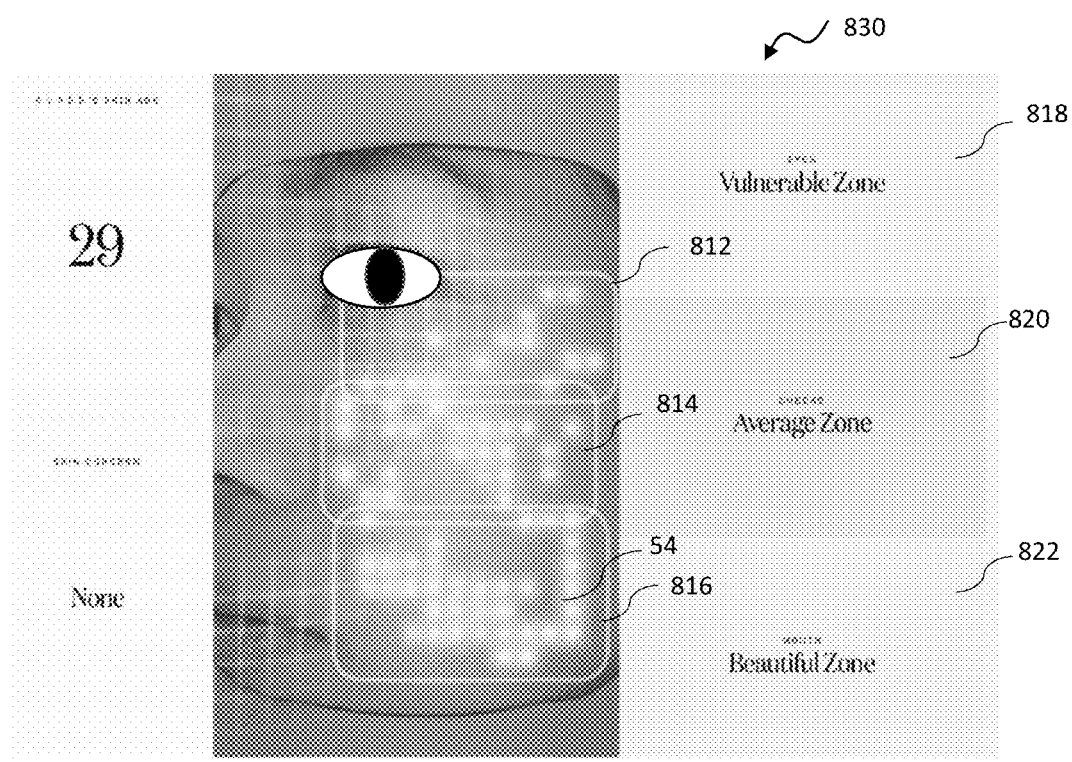
FIG. 22 is an exemplary user interface for visualizing a cosmetic skin attribute according to the present invention.

FIG. 22 is a screen shot of an exemplary user interface 830 for displaying a cosmetic skin attribute. Specifically, the user interface 830 has substantially the same features as the user interface 820 of FIG. 21 and differs in that the tiles 54 in each of the three ROI 812, 814, 816 are displayed. It will be appreciated that the tiles 54 may be configured to be displayed in a single ROI such as for example displaying ROI 816 only wherein ROI 816 is indicative of a beautiful zone based on the image description 822.

Figure 23:
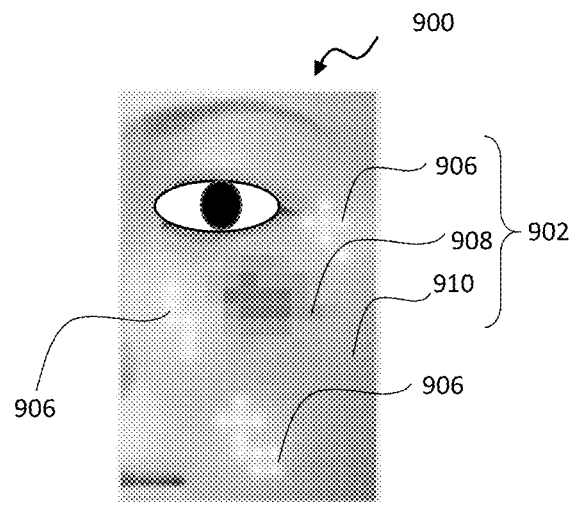
FIG. 23 is a screen shot illustrating an exemplary user interface comprising a heat map as an example of an image description for visualizing at least one cosmetic skin attribute according to the present invention.

FIG. 23 depicts a partial view of an exemplary user interface 900 comprising an image description 901 overlaid on a digital image 51 for visualizing at least one cosmetic skin attribute according to the present invention. The image description 902 comprises a heat map generated based on the entropy values output from the method 500 described hereinbefore. The heat map comprises a first heat map section 906 based on low entropy values which correspond to a better cosmetic skin attribute condition. The heat map 904 further comprises a second heat map section 908 based on high entropy values correspond to a poorer cosmetic skin attribute condition. The first heat map section 906 is formed of a first plurality of tiles which is visually different from a second plurality of tiles in the second heat map section 908. For example, the first plurality of tiles is converted to display a different color from the color of the second plurality of tiles. Heat map sections 910 which are not displayed (hereinafter "non-displayed heat map sections 910") correspond to entropy values between the high and low entropy values. The heat map sections may be configured as follows to display entropy information related to the cosmetic skin attribute condition and the Skin Attribute Index as outlined in Table 5 below.

TABLE 5

| Heat Map | Heat Map Section Visualization | Entropy Values | Cosmetic Skin Attribute Condition |
|---|---|---|---|
| Heat Map Section 906 | Displayed as first color | Low | Better |
| Heat Map Section 908 | Displayed as second color different from first color | High | Poor |
| Heat Map Section 910 | Not Displayed | Between Low and High | Between Poor and Better |

Figure 24:
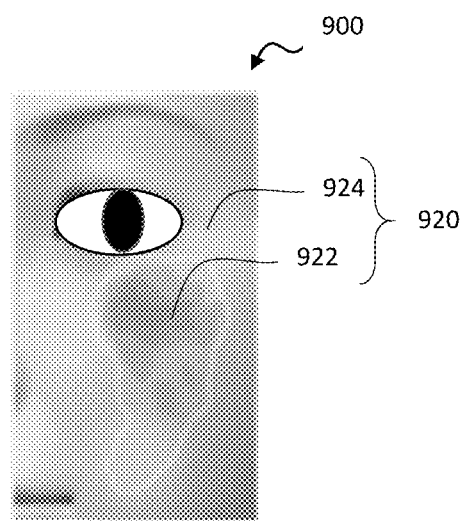
FIG. 24 is a screen shot illustrating an alternate variation of an image description for visualizing at least one cosmetic skin attribute in the user interface of FIG. 23.

FIG. 24 depicts an alternate variation of an image description 920 for visualizing at least one cosmetic skin attribute in the user interface 900 of FIG. 23. The image description 920 differs from the image description 902 of FIG. 19 in that the image description 920 comprises a displayed region of interest (ROI) 922 wherein the displayed ROI 922 is converted to display a color to indicate poorer cosmetic skin attribute condition relative to other non-displayed regions of interest (ROI) 924 which correspond to better cosmetic skin attribute condition. An advantage of only displaying a single heat map section (see FIG. 20) or ROI is that the consumer viewing the user interface is not overloaded with too much visual information.

FIG. 25 is a screen shot illustrating an exemplary user interface 930 for visualizing at least one cosmetic skin attribute according to the present invention, wherein the at least one cosmetic skin attribute is skin purity. The user interface 930 differs from the user interface 902 of FIG. 19 in that the user interface 930 comprises alternate text 932 describing the cosmetic skin attribute and an aggregate score 934 based on the generated Skin Attribute Index. The user interface 930 may further comprise a meter 936 and a meter marker 938 for representing the aggregate score on a scale of 0 to 100 along the meter 936. The meter 936 is a different way of visualizing the aggregate score 934, and may be optional. A color of the meter 936 may be configured to show a gradient of colors representative of the first heat map section 904 and the second heat map section 906.

The methods for determining a cosmetic skin condition according the present invention described hereinbefore may further comprise a step of tracking the cosmetic skin attribute over a predetermined period of time. For example, the user interface 930 as shown in FIG. 21 may comprise a first selectable icon 940 which upon selection, causes instructions to be received by and steps performed by the processor to generate a calendar or schedule to create a cosmetic skin attribute diary to track improvement of cosmetic skin attributes. For example, when the consumer uses it on Day 1, the date and facial analysis is recorded and saved in the memory. Subsequently, whenever the consumer uses the method according to the present invention in future (after a predetermined period, 1 week, 1 month, 6 months), the facial skin of the consumer is analyzed again and the consumer can compare how his/her facial skin looks at the time after the predetermined period relative to Day 1. The methods according to the present invention may be configured to be a downloadable software application that is stored as a native application on a portable electronic device or a web application that can be accessed through a login account specific to a consumer, so that the consumer can perform a self-skin analysis based on the methods according to the present invention and view and/or monitor the improvement (reduction in the ROIs with poorer cosmetic skin attribute condition) over a period of time.

The user interface 930 may further comprise a second selectable icon 942 which upon selection, enables the method for determining a cosmetic skin attribute according to the present invention to be repeated. For example, the method 500 described hereinbefore may be repeated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of visualizing at least one cosmetic skin attribute of a subject, the method comprising the steps of, in the following order:
   a) obtaining a first digital image of at least a portion of a face of the subject, wherein the first digital image is selected from at least an area of an input image of the face;
   b) defining a plurality of tiles across the obtained first digital image, wherein the plurality of tiles are adjacent so as to define a tile map; wherein each tile comprises a height and a width not greater than 100 by 100 pixels;
   c) analyzing the first digital image for each of the defined plurality of tiles for the at least one cosmetic skin attribute;

d) assigning a single degree of indicium uniquely to each tile, of the defined plurality of tiles, based on the analyzed at least one cosmetic skin attributes of the tile; and e) displaying at least some of the plurality of tiles each having uniquely assigned single degree of indicium to visualize at least one cosmetic skin attribute;

wherein the displayed at least some of the plurality of tiles displays a cosmetic skin attribute condition that is better relative to a cosmetic skin attribute condition of a non-displayed tile of the plurality of tiles based on the analyzed at least one cosmetic skin attribute of the tile.

2. The method of claim 1, wherein the displayed plurality of tiles comprises a first displayed tile and a second displayed tile, wherein there is a visual difference between the first displayed tile and the second displayed tile, wherein the first displayed tile displays a cosmetic skin attribute condition that is better than a cosmetic skin attribute condition of the second displayed tile based on at least one analyzed cosmetic skin attribute of the tile.

3. The method of claim 1, wherein the obtained first digital image comprises at least one region of interest (ROI) selected from the group consisting of a skin region around the eye ("eye region"), a skin region around the cheek ("cheek region"), a skin region around the mouth ("mouth region"), and combinations thereof.

4. The method according to claim 3, wherein displaying in step (e) comprises displaying the region of interest (ROI) based on the plurality of tiles each having uniquely assigned single degree of indicium.

5. The method of claim 1, further comprising displaying a comparison between the single degree of indicium for each tile of the defined plurality of tiles and a predetermined value associated with a defined population of people.

6. The method of claim 1, wherein displaying in step (e) comprises interposing a second digital image of at least a portion of a face of the subject and said displayed plurality of tiles each having uniquely assigned single degree of indicium.

7. The method according to claim 1, wherein the cosmetic skin attribute is selected from the group consisting of skin purity, skin age, skin topography, skin tone, skin pigmentation, skin pores, skin inflammation, skin hydration, skin sebum level, acne, moles, skin radiance, skin shine, skin dullness, and skin barrier.

8. The method according to claim 1, wherein the cosmetic skin attribute is a visually imperceivable cosmetic skin attribute that is not detectable by an unaided eye or a cosmetic skin attribute detectable visually by a consumer, but the consumer does not understand the cosmetic skin attribute.

9. The method according to claim 1, wherein the single degree of indicium is selected from the group consisting of a graphical symbol, a numerical value, a color code, illumination and combinations thereof.

10. The method of claim 1, further comprising displaying at least one product recommendation item to treat the displayed cosmetic skin attribute.

11. The method of claim 1, wherein in step (c) of analyzing, a Skin Attribute Index is generated as a probability value indicative of a condition of the cosmetic skin attribute of the at least one portion of skin of the subject relative to a defined population of people, preferably the Skin Attribute Index is generated as a function of an entropy value defined by F(Entropy Value), wherein said function is determined by a model established upon a training dataset wherein the training dataset comprises: (i) a plurality of color channel images of the defined population of people, wherein each of the plurality of color channel images comprises facial skin of a person in the defined population of people, wherein the facial skin comprises the cosmetic skin attribute; (ii) an associated class definition based on the cosmetic skin attribute.

12. The method of claim 11, wherein the age of the subject and the average age of the defined population of people is each independently from 18 to 60 years, preferably from 20 to 40 years, more preferably 25 to 35 years, even more preferably 28 to 32 years.

13. A method of visualizing at least one cosmetic skin attribute of a subject, the method comprising the steps of:

a) displaying a first digital image of at least a portion of a face of the subject;

b) interposing a second digital image of at least a portion of a face of the subject and a plurality of tiles each having uniquely assigned single degree of indicium; wherein the plurality of tiles are adjacent so as to define a tile map; and c) displaying at least one region of interest (ROI) of the at least a portion of a face of the subject based on the plurality of tiles; wherein each tile comprises a height and a width not greater than 100 by 100 pixels; wherein each tile comprises a having uniquely assigned single degree of indicium on the second digital image, wherein the at least one ROI is selected from the group consisting of: a skin region around the eye, a skin region around the cheek, a skin region around the mouth, and combinations thereof; wherein displaying comprises displaying two or three ROI, wherein one of the two or three ROIs has a different boundary line from each of the other ones of the two or three ROIs, wherein the displayed boundary line of the at least one of the three ROI is indicative of the at least one of the two or three ROI having a cosmetic skin attribute condition that is better relative to a cosmetic skin attribute of each of the other ones of the two or three ROI.

14. A graphical user interface for providing a product recommendation to treat at least one cosmetic skin attribute, the graphical user interface being on a portable electronic apparatus including a touch screen display/display with an input device and an image obtaining device, the graphical user interface comprising:

a first area of the touch screen display displaying a first digital image of at least a portion of a face of the subject obtained from the image obtaining device and a second digital image interposed on the first digital image, the second digital image having the at least a portion of a face of the subject and said displayed plurality of adjacent tiles defining a tile map; wherein each tile comprises a uniquely assigned single degree of indicium; wherein each tile comprises a height and a width not greater than 100 by 100 pixels; and a second area of the touch screen display different from the first area, the second area displaying a selectable icon for receiving a user input, wherein an image of at least one product recommendation item to treat the displayed cosmetic skin attribute is displayed on the touch screen display if the user activates the selectable icon.

15. The graphical user interface according to claim 14, wherein the at least one cosmetic skin attribute is a visually imperceivable cosmetic skin attribute, wherein the visually imperceivable cosmetic skin attribute is a cosmetic skin attribute which is not detectable by an unaided eye, or a cosmetic skin attribute detectable visually by a consumer but the consumer does not understand the cosmetic skin attribute.

\* \* \* \* \*